US007909869B2

(12) United States Patent
Gordon et al.

(10) Patent No.: US 7,909,869 B2
(45) Date of Patent: Mar. 22, 2011

(54) ARTIFICIAL SPINAL UNIT ASSEMBLIES

(75) Inventors: Charles R. Gordon, Tyler, TX (US);
Corey T. Harbold, Tyler, TX (US);
Heather S. Hanson, San Antonio, TX (US)

(73) Assignee: Flexuspine, Inc., Pittsburg, PA (US)

( * ) Notice: Subject to any disclaimer, the term of this patent is extended or adjusted under 35 U.S.C. 154(b) by 686 days.

(21) Appl. No.: 10/777,411

(22) Filed: Feb. 12, 2004

(65) Prior Publication Data
US 2005/0033432 A1 Feb. 10, 2005

Related U.S. Application Data

(63) Continuation-in-part of application No. 10/634,950, filed on Aug. 5, 2003, now Pat. No. 7,204,853.

(51) Int. Cl.
*A61F 2/44* (2006.01)
(52) U.S. Cl. .................................................. 623/17.11
(58) Field of Classification Search ...... 623/17.11–17.16
See application file for complete search history.

(56) References Cited

U.S. PATENT DOCUMENTS

| 3,848,601 A | 11/1974 | Ma et al. |
| 3,867,728 A | 2/1975 | Stubstad et al. |
| 4,309,777 A | 1/1982 | Patil |
| 4,349,921 A | 9/1982 | Kuntz |
| 4,611,581 A | 9/1986 | Steffee |
| 4,657,550 A | 4/1987 | Daher |
| 4,696,290 A | 9/1987 | Steffee |
| 4,743,260 A | 5/1988 | Burton |
| 4,759,766 A | 7/1988 | Buettner-Janz et al. |
| 4,759,769 A | 7/1988 | Hedman et al. |
| 4,772,287 A | 9/1988 | Ray et al. |
| 4,854,311 A | 8/1989 | Steffee |
| 4,863,476 A * | 9/1989 | Shepperd ............... 623/17.15 |

(Continued)

FOREIGN PATENT DOCUMENTS
FR 2716616 9/1995
(Continued)

OTHER PUBLICATIONS

Invitation to Pay Additional Fees From the International Searching Authority for PCT/US2004/025090 mailed on Dec. 7, 2004 (8 pages).

(Continued)

*Primary Examiner* — David Isabella
*Assistant Examiner* — Ann Schillinger
(74) *Attorney, Agent, or Firm* — Meyertons, Hood, Kivlin, Kowert & Goetzel, P.C.; Eric B. Meyertons

(57) ABSTRACT

An artificial functional spinal unit is provided comprising, generally, an expandable artificial intervertebral implant that can be placed via a posterior surgical approach and used in conjunction with one or more artificial facet joints to provide an anatomically correct range of motion. Expandable artificial intervertebral implants in both lordotic and non-lordotic designs are disclosed, as well as lordotic and non-lordotic expandable cages for both PLIF (posterior lumber interbody fusion) and TLIF (transforaminal lumbar interbody fusion) procedures. The expandable implants may have various shapes, such as round, square, rectangular, banana-shaped, kidney-shaped, or other similar shapes. By virtue of their posteriorly implanted approach, the disclosed artificial FSU's allow for posterior decompression of the neural elements, reconstruction of all or part of the natural functional spinal unit, restoration and maintenance of lordosis, maintenance of motion, and restoration and maintenance of disc space height.

38 Claims, 25 Drawing Sheets

U.S. PATENT DOCUMENTS

| | | |
|---|---|---|
| 4,863,477 A | 9/1989 | Monson |
| 4,907,577 A | 3/1990 | Wu |
| 4,911,718 A | 3/1990 | Lee et al. |
| 4,932,975 A | 6/1990 | Main et al. |
| 4,946,378 A | 8/1990 | Hirayama et al. |
| 4,946,458 A | 8/1990 | Harms et al. |
| 5,042,982 A | 8/1991 | Harms et al. |
| 5,047,055 A | 9/1991 | Bao et al. |
| 5,059,194 A | 10/1991 | Michelson |
| 5,071,437 A | 12/1991 | Steffee |
| 5,092,867 A | 3/1992 | Harms et al. |
| 5,108,438 A | 4/1992 | Stone |
| 5,123,926 A | 6/1992 | Pisharodi |
| 5,171,278 A * | 12/1992 | Pisharodi ................. 128/898 |
| 5,171,281 A | 12/1992 | Parsons et al. |
| 5,180,393 A | 1/1993 | Commarmond |
| 5,192,326 A | 3/1993 | Bao et al. |
| 5,196,013 A | 3/1993 | Harms et al. |
| 5,207,678 A | 5/1993 | Harms et al. |
| 5,246,458 A | 9/1993 | Graham |
| 5,258,031 A | 11/1993 | Salib et al. |
| 5,261,909 A | 11/1993 | Sutterlin et al. |
| 5,306,307 A | 4/1994 | Senter et al. |
| 5,306,309 A | 4/1994 | Wagner et al. |
| 5,314,477 A * | 5/1994 | Marnay ................. 623/17.15 |
| 5,320,644 A | 6/1994 | Baumgartner |
| 5,336,223 A | 8/1994 | Rogers |
| 5,370,697 A | 12/1994 | Baumgartner |
| 5,375,823 A * | 12/1994 | Navas ................. 623/17.15 |
| 5,397,364 A | 3/1995 | Kozak et al. |
| 5,401,269 A | 3/1995 | Buettner-Janz et al. |
| 5,403,315 A | 4/1995 | Ashman |
| 5,415,661 A | 5/1995 | Holmes |
| 5,423,816 A | 6/1995 | Lin |
| 5,425,773 A | 6/1995 | Boyd et al. |
| 5,443,467 A | 8/1995 | Biedermann et al. |
| 5,458,642 A | 10/1995 | Beer et al. |
| 5,458,643 A | 10/1995 | Oka et al. |
| 5,496,321 A | 3/1996 | Puno et al. |
| 5,498,263 A | 3/1996 | DiNello et al. |
| 5,514,132 A | 5/1996 | Csernatony et al. |
| 5,514,180 A | 5/1996 | Heggeness et al. |
| 5,522,899 A | 6/1996 | Michelson |
| 5,534,028 A | 7/1996 | Bao et al. |
| 5,534,029 A | 7/1996 | Shima |
| 5,534,030 A | 7/1996 | Navarro et al. |
| 5,545,165 A | 8/1996 | Biedermann et al. |
| 5,556,431 A | 9/1996 | Buettner-Janz |
| 5,562,663 A | 10/1996 | Wisnewski et al. |
| 5,562,737 A | 10/1996 | Graf |
| 5,562,738 A | 10/1996 | Boyd et al. |
| 5,571,109 A | 11/1996 | Bertagnoli |
| 5,645,599 A | 7/1997 | Samani |
| 5,653,763 A | 8/1997 | Errico et al. |
| 5,665,122 A * | 9/1997 | Kambin ................. 623/17.16 |
| 5,672,176 A | 9/1997 | Biedermann et al. |
| 5,674,294 A | 10/1997 | Bainville et al. |
| 5,674,296 A | 10/1997 | Bryan et al. |
| 5,676,701 A | 10/1997 | Yuan et al. |
| 5,676,702 A | 10/1997 | Ratron |
| 5,683,391 A | 11/1997 | Boyd |
| 5,683,464 A | 11/1997 | Wagner et al. |
| 5,683,465 A | 11/1997 | Shinn et al. |
| 5,702,450 A | 12/1997 | Bisserie |
| 5,725,527 A | 3/1998 | Biedermann et al. |
| 5,733,284 A | 3/1998 | Martin |
| 5,741,253 A | 4/1998 | Michelson |
| 5,755,797 A | 5/1998 | Baumgartner |
| 5,776,199 A | 7/1998 | Michelson |
| 5,782,832 A * | 7/1998 | Larsen et al. ................. 606/61 |
| 5,785,647 A | 7/1998 | Tompkins et al. |
| 5,797,909 A | 8/1998 | Michelson |
| 5,800,549 A | 9/1998 | Bao et al. |
| 5,800,550 A * | 9/1998 | Sertich ................. 623/17.16 |
| 5,810,819 A * | 9/1998 | Errico et al. ................. 606/61 |
| 5,824,093 A | 10/1998 | Ray et al. |
| 5,824,094 A | 10/1998 | Serhan et al. |
| 5,827,328 A | 10/1998 | Buttermann |
| 5,861,041 A | 1/1999 | Tienboon |
| 5,863,293 A | 1/1999 | Richelsoph |
| 5,865,846 A | 2/1999 | Bryan et al. |
| 5,865,848 A | 2/1999 | Baker |
| 5,888,220 A | 3/1999 | Felt et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,928,243 A | 7/1999 | Guyer |
| 5,935,133 A | 8/1999 | Wagner et al. |
| 5,938,663 A | 8/1999 | Petreto |
| 5,951,555 A | 9/1999 | Rehak et al. |
| 5,961,518 A | 10/1999 | Errico et al. |
| 5,961,554 A | 10/1999 | Janson et al. |
| 5,964,769 A | 10/1999 | Wagner et al. |
| 5,976,186 A | 11/1999 | Bao et al. |
| 5,984,967 A | 11/1999 | Zdeblick et al. |
| 5,989,250 A | 11/1999 | Wagner et al. |
| 5,989,290 A | 11/1999 | Biedermann et al. |
| 5,997,539 A | 12/1999 | Errico et al. |
| 6,001,130 A | 12/1999 | Bryan et al. |
| 6,017,344 A | 1/2000 | Errico et al. |
| 6,019,792 A | 2/2000 | Cauthen |
| 6,022,376 A | 2/2000 | Assell et al. |
| 6,030,389 A | 2/2000 | Wagner et al. |
| 6,039,763 A | 3/2000 | Shelokov |
| 6,045,579 A * | 4/2000 | Hochshuler et al. ........ 623/17.16 |
| 6,053,921 A | 4/2000 | Wagner et al. |
| 6,063,089 A | 5/2000 | Errico et al. |
| RE36,758 E | 6/2000 | Fitz |
| 6,080,193 A | 6/2000 | Hochschuler et al. |
| 6,093,205 A | 7/2000 | McLeod et al. |
| 6,096,038 A | 8/2000 | Michelson |
| 6,102,950 A * | 8/2000 | Vaccaro ................. 623/17.16 |
| 6,106,526 A | 8/2000 | Harms et al. |
| 6,110,210 A | 8/2000 | Norton et al. |
| 6,113,637 A | 9/2000 | Gill et al. |
| 6,123,707 A | 9/2000 | Wagner et al. |
| 6,126,689 A | 10/2000 | Brett |
| 6,132,430 A | 10/2000 | Wagner et al. |
| 6,132,464 A | 10/2000 | Martin |
| 6,132,465 A | 10/2000 | Ray et al. |
| 6,136,031 A | 10/2000 | Middleton |
| 6,139,579 A | 10/2000 | Steffee et al. |
| 6,146,421 A | 11/2000 | Gordon et al. |
| 6,146,422 A | 11/2000 | Lawson |
| 6,156,067 A | 12/2000 | Bryan et al. |
| 6,162,252 A | 12/2000 | Kuras et al. |
| 6,165,218 A | 12/2000 | Husson et al. |
| 6,176,882 B1 | 1/2001 | Biedermann et al. |
| 6,179,874 B1 | 1/2001 | Cauthen |
| 6,187,048 B1 | 2/2001 | Milner et al. |
| 6,200,348 B1 | 3/2001 | Biedermann et al. |
| 6,206,924 B1 | 3/2001 | Timm |
| 6,214,049 B1 | 4/2001 | Gayer et al. |
| 6,214,050 B1 * | 4/2001 | Huene ................. 623/17.15 |
| 6,217,579 B1 | 4/2001 | Koros |
| 6,228,118 B1 | 5/2001 | Gordon |
| 6,231,609 B1 * | 5/2001 | Mehdizadeh ............. 623/17.11 |
| 6,241,730 B1 | 6/2001 | Alby |
| 6,264,656 B1 | 7/2001 | Michelson |
| 6,290,724 B1 | 9/2001 | Marino |
| 6,296,664 B1 | 10/2001 | Middleton |
| 6,315,797 B1 | 11/2001 | Middleton |
| 6,331,179 B1 | 12/2001 | Freid et al. |
| 6,348,071 B1 | 2/2002 | Steffee et al. |
| RE37,665 E | 4/2002 | Ralph et al. |
| 6,368,350 B1 | 4/2002 | Erickson et al. |
| 6,368,351 B1 * | 4/2002 | Glenn et al. ................. 623/17.15 |
| 6,371,990 B1 | 4/2002 | Ferree |
| 6,375,682 B1 * | 4/2002 | Fleischmann et al. ...... 623/17.12 |
| 6,375,683 B1 | 4/2002 | Crozet et al. |
| 6,391,090 B1 | 5/2002 | Wagner et al. |
| 6,395,032 B1 | 5/2002 | Gauchet |
| 6,395,034 B1 | 5/2002 | Suddaby |
| 6,402,784 B1 | 6/2002 | Wardlaw |
| 6,402,785 B1 | 6/2002 | Zdeblick et al. |

| Patent Number | Date | Inventor |
|---|---|---|
| 6,409,766 B1 | 6/2002 | Brett |
| 6,413,259 B1 | 7/2002 | Lyons et al. |
| 6,416,515 B1 | 7/2002 | Wagner et al. |
| 6,419,703 B1 | 7/2002 | Fallin et al. |
| 6,419,704 B1 | 7/2002 | Ferree |
| 6,436,140 B1 * | 8/2002 | Liu et al. .................. 623/17.11 |
| 6,440,168 B1 | 8/2002 | Cauthen |
| 6,442,814 B1 | 9/2002 | Landry et al. |
| 6,443,990 B1 | 9/2002 | Aebi et al. |
| 6,447,512 B1 | 9/2002 | Landry et al. |
| 6,447,544 B1 | 9/2002 | Michelson |
| 6,451,021 B1 | 9/2002 | Ralph et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,478,822 B1 | 11/2002 | Leroux et al. |
| 6,478,823 B1 | 11/2002 | Michelson |
| 6,482,207 B1 | 11/2002 | Errico |
| 6,482,234 B1 | 11/2002 | Weber et al. |
| 6,488,710 B2 | 12/2002 | Besselink |
| 6,500,205 B1 | 12/2002 | Michelson |
| 6,520,996 B1 | 2/2003 | Manasas et al. |
| 6,524,312 B2 | 2/2003 | Landry et al. |
| 6,533,817 B1 * | 3/2003 | Norton et al. .............. 623/17.16 |
| 6,533,818 B1 | 3/2003 | Weber et al. |
| 6,540,748 B2 | 4/2003 | Lombardo |
| 6,558,423 B1 | 5/2003 | Michelson |
| 6,562,040 B1 | 5/2003 | Wagner et al. |
| 6,562,074 B2 | 5/2003 | Gerbec et al. |
| 6,565,566 B1 | 5/2003 | Wagner et al. |
| 6,565,605 B2 | 5/2003 | Goble et al. |
| 6,569,442 B2 | 5/2003 | Gan et al. |
| 6,572,653 B1 | 6/2003 | Simonson |
| 6,576,016 B1 | 6/2003 | Hochschuler et al. |
| 6,579,318 B2 | 6/2003 | Varga et al. |
| 6,579,319 B2 | 6/2003 | Goble et al. |
| 6,582,467 B1 | 6/2003 | Teitelbaum et al. |
| 6,595,992 B1 | 7/2003 | Wagner et al. |
| 6,595,998 B2 | 7/2003 | Johnson et al. |
| 6,610,091 B1 | 8/2003 | Reiley |
| 6,610,094 B2 | 8/2003 | Husson |
| 6,613,050 B1 | 9/2003 | Wagner et al. |
| 6,616,671 B2 | 9/2003 | Landry et al. |
| 6,626,904 B1 | 9/2003 | Jammet et al. |
| 6,626,905 B1 | 9/2003 | Schmeil et al. |
| 6,635,062 B2 | 10/2003 | Ray et al. |
| 6,641,614 B1 | 11/2003 | Wagner et al. |
| 6,648,893 B2 | 11/2003 | Dudasik |
| 6,648,915 B2 | 11/2003 | Sazy |
| 6,648,917 B2 | 11/2003 | Gerbec et al. |
| 6,666,870 B2 | 12/2003 | Dixon |
| 6,666,891 B2 * | 12/2003 | Boehm et al. .............. 623/17.16 |
| 6,679,915 B1 | 1/2004 | Cauthen |
| 6,682,533 B1 | 1/2004 | Dinsdale et al. |
| 6,685,742 B1 * | 2/2004 | Jackson ...................... 623/17.11 |
| 6,692,495 B1 | 2/2004 | Zacouto |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,796 B2 | 4/2004 | Cohen et al. |
| 6,733,531 B1 | 5/2004 | Trieu |
| 6,736,850 B2 | 5/2004 | Davis |
| 6,743,257 B2 | 6/2004 | Castro |
| 6,758,861 B2 | 7/2004 | Ralph et al. |
| 6,802,844 B2 | 10/2004 | Ferree |
| 6,811,567 B2 | 11/2004 | Reiley |
| 6,821,298 B1 * | 11/2004 | Jackson ...................... 623/17.15 |
| 6,852,129 B2 | 2/2005 | Gerbec et al. |
| 6,863,673 B2 | 3/2005 | Gerbec et al. |
| D505,205 S | 5/2005 | Freid |
| 6,893,464 B2 * | 5/2005 | Kiester ...................... 623/17.11 |
| 6,902,580 B2 | 6/2005 | Fallin et al. |
| 6,928,284 B2 | 8/2005 | Palat et al. |
| 6,936,070 B1 | 8/2005 | Muhanna |
| 6,953,477 B2 | 10/2005 | Berry |
| 6,962,606 B2 | 11/2005 | Michelson |
| 6,964,664 B2 | 11/2005 | Freid et al. |
| 6,966,929 B2 | 11/2005 | Mitchell |
| 6,966,930 B2 | 11/2005 | Arnin et al. |
| 6,974,478 B2 | 12/2005 | Reiley et al. |
| 6,981,989 B1 * | 1/2006 | Fleischmann et al. ...... 623/17.11 |
| 6,991,632 B2 | 1/2006 | Ritland |
| 6,994,727 B2 | 2/2006 | Khandkar et al. |
| 6,997,929 B2 | 2/2006 | Manzi et al. |
| 7,011,685 B2 | 3/2006 | Arnin et al. |
| 7,018,415 B1 | 3/2006 | McKay |
| 7,029,475 B2 | 4/2006 | Panjabi |
| 7,083,622 B2 | 8/2006 | Simonson |
| 7,083,649 B2 | 8/2006 | Zucherman et al. |
| 7,090,698 B2 | 8/2006 | Goble et al. |
| 7,101,398 B2 | 9/2006 | Dooris et al. |
| 7,118,579 B2 | 10/2006 | Michelson |
| 7,118,580 B1 | 10/2006 | Beyersdorff et al. |
| 7,128,760 B2 | 10/2006 | Michelson |
| 7,147,664 B2 | 12/2006 | Louis et al. |
| 7,153,310 B2 | 12/2006 | Ralph et al. |
| 7,204,853 B2 | 4/2007 | Gordon et al. |
| 7,273,496 B2 | 9/2007 | Mitchell |
| 7,291,150 B2 | 11/2007 | Graf |
| 7,291,159 B2 | 11/2007 | Graf |
| 7,311,713 B2 | 12/2007 | Johnson et al. |
| 7,316,714 B2 | 1/2008 | Gordon et al. |
| 7,320,707 B2 | 1/2008 | Zucherman |
| 7,338,525 B2 | 3/2008 | Ferree |
| 7,364,589 B2 | 4/2008 | Eisermann |
| 7,473,276 B2 | 1/2009 | Aebi et al. |
| 7,476,238 B2 | 1/2009 | Panjabi |
| 7,517,359 B2 | 4/2009 | Drewry et al. |
| 7,547,309 B2 | 6/2009 | Bertagnoli et al. |
| 7,550,009 B2 | 6/2009 | Arnin et al. |
| 7,615,068 B2 | 11/2009 | Timm et al. |
| 7,635,379 B2 | 12/2009 | Callahan et al. |
| 7,699,875 B2 | 4/2010 | Timm et al. |
| 7,708,778 B2 | 5/2010 | Gordon et al. |
| 7,713,287 B2 | 5/2010 | Timm et al. |
| 7,713,288 B2 | 5/2010 | Timm et al. |
| 7,753,958 B2 | 7/2010 | Gordon et al. |
| 7,785,351 B2 | 8/2010 | Gordon et al. |
| 7,794,480 B2 | 9/2010 | Gordon et al. |
| 7,799,082 B2 | 9/2010 | Gordon et al. |
| 2001/0020476 A1 | 9/2001 | Gan et al. |
| 2001/0032020 A1 | 10/2001 | Besselink |
| 2002/0040243 A1 * | 4/2002 | Attali et al. ................. 623/17.16 |
| 2002/0065557 A1 | 5/2002 | Goble et al. |
| 2002/0068977 A1 * | 6/2002 | Jackson ..................... 623/17.15 |
| 2002/0072801 A1 | 6/2002 | Michelson |
| 2002/0082701 A1 | 6/2002 | Zdeblick et al. |
| 2002/0091390 A1 | 7/2002 | Michelson |
| 2002/0095154 A1 | 7/2002 | Atkinson et al. |
| 2002/0123806 A1 | 9/2002 | Reiley |
| 2002/0128659 A1 | 9/2002 | Michelson |
| 2002/0128714 A1 | 9/2002 | Manasas et al. |
| 2002/0130112 A1 | 9/2002 | Manasas et al. |
| 2002/0143401 A1 | 10/2002 | Michelson |
| 2003/0028250 A1 | 2/2003 | Reiley et al. |
| 2003/0040802 A1 | 2/2003 | Errico |
| 2003/0055427 A1 | 3/2003 | Graf |
| 2003/0069643 A1 | 4/2003 | Ralph et al. |
| 2003/0074063 A1 | 4/2003 | Gerbec et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 * | 4/2003 | Errico et al. ................. 623/17.14 |
| 2003/0074074 A1 | 4/2003 | Errico et al. |
| 2003/0135275 A1 | 7/2003 | Garcia et al. |
| 2003/0135277 A1 | 7/2003 | Bryan et al. |
| 2003/0139812 A1 | 7/2003 | Garcia et al. |
| 2003/0149483 A1 | 8/2003 | Michelson |
| 2003/0176923 A1 | 9/2003 | Keller et al. |
| 2003/0191470 A1 | 10/2003 | Ritland |
| 2003/0204259 A1 | 10/2003 | Goble et al. |
| 2003/0204260 A1 | 10/2003 | Ferree |
| 2003/0220643 A1 | 11/2003 | Ferree |
| 2003/0225409 A1 | 12/2003 | Freid et al. |

| | | | | | | |
|---|---|---|---|---|---|---|
| 2003/0233145 A1 | 12/2003 | Landry et al. | | 2005/0256578 A1 | 11/2005 | Blatt et al. |
| 2004/0006391 A1 | 1/2004 | Reiley | | 2005/0273167 A1 | 12/2005 | Triplett et al. |
| 2004/0019353 A1 | 1/2004 | Freid et al. | | 2005/0273171 A1 | 12/2005 | Gordon et al. |
| 2004/0030387 A1 | 2/2004 | Landry et al. | | 2005/0273173 A1 | 12/2005 | Gordon et al. |
| 2004/0030389 A1 | 2/2004 | Ferree | | 2005/0273174 A1 | 12/2005 | Gordon et al. |
| 2004/0039448 A1 | 2/2004 | Pisharodi | | 2005/0273175 A1 | 12/2005 | Gordon et al. |
| 2004/0044411 A1 | 3/2004 | Suddaby | | 2005/0278026 A1 | 12/2005 | Gordon et al. |
| 2004/0049190 A1 | 3/2004 | Biedermann et al. | | 2005/0283244 A1 | 12/2005 | Gordon et al. |
| 2004/0049271 A1* | 3/2004 | Biedermann et al. ...... 623/17.11 | | 2005/0283245 A1 | 12/2005 | Gordon et al. |
| 2004/0049272 A1 | 3/2004 | Reiley | | 2005/0283247 A1 | 12/2005 | Gordon et al. |
| 2004/0049273 A1 | 3/2004 | Reiley | | 2005/0283248 A1 | 12/2005 | Gordon et al. |
| 2004/0049274 A1 | 3/2004 | Reiley | | 2005/0288670 A1 | 12/2005 | Panjabi et al. |
| 2004/0049275 A1 | 3/2004 | Reiley | | 2006/0009768 A1 | 1/2006 | Ritland |
| 2004/0049276 A1 | 3/2004 | Reiley | | 2006/0009850 A1 | 1/2006 | Frigg et al. |
| 2004/0049277 A1 | 3/2004 | Reiley | | 2006/0015100 A1 | 1/2006 | Panjabi et al. |
| 2004/0049278 A1 | 3/2004 | Reiley | | 2006/0036240 A1 | 2/2006 | Colleran |
| 2004/0049280 A1 | 3/2004 | Cauthen | | 2006/0036245 A1 | 2/2006 | Stern |
| 2004/0049281 A1 | 3/2004 | Reiley | | 2006/0084986 A1 | 4/2006 | Grinberg et al. |
| 2004/0087947 A1 | 5/2004 | Lim et al. | | 2006/0089717 A1 | 4/2006 | Krishna et al. |
| 2004/0093083 A1 | 5/2004 | Branch et al. | | 2006/0095132 A1 | 5/2006 | Kirschman |
| 2004/0102774 A1 | 5/2004 | Trieu | | 2006/0129244 A1 | 6/2006 | Ensign |
| 2004/0106997 A1 | 6/2004 | Lieberson | | 2006/0142759 A1 | 6/2006 | Arnin et al. |
| 2004/0117020 A1 | 6/2004 | Frey et al. | | 2006/0149228 A1 | 7/2006 | Schlapfer et al. |
| 2004/0127989 A1 | 7/2004 | Dooris et al. | | 2006/0149229 A1 | 7/2006 | Kwak et al. |
| 2004/0133278 A1 | 7/2004 | Marino et al. | | 2006/0149278 A1 | 7/2006 | Abdou |
| 2004/0133281 A1 | 7/2004 | Khandkar et al. | | 2006/0149383 A1 | 7/2006 | Arnin et al. |
| 2004/0138662 A1 | 7/2004 | Landry et al. | | 2006/0167547 A1 | 7/2006 | Suddaby |
| 2004/0138749 A1 | 7/2004 | Zucherman | | 2006/0189983 A1 | 8/2006 | Fallin et al. |
| 2004/0143265 A1 | 7/2004 | Landry et al. | | 2006/0195114 A1 | 8/2006 | Bertagnoli |
| 2004/0143332 A1 | 7/2004 | Krueger et al. | | 2006/0195191 A1 | 8/2006 | Sweeney et al. |
| 2004/0147928 A1 | 7/2004 | Landry et al. | | 2006/0195192 A1 | 8/2006 | Gordon et al. |
| 2004/0153065 A1 | 8/2004 | Lim | | 2006/0229729 A1 | 10/2006 | Gordon |
| 2004/0167626 A1 | 8/2004 | Geremakis et al. | | 2006/0241642 A1 | 10/2006 | Arnin et al. |
| 2004/0172134 A1* | 9/2004 | Berry ........................ 623/17.11 | | 2006/0241770 A1 | 10/2006 | Rhoda et al. |
| 2004/0181223 A1 | 9/2004 | Ritland | | 2006/0260483 A1 | 11/2006 | Hartmann et al. |
| 2004/0181284 A1 | 9/2004 | Simonson | | 2006/0264937 A1 | 11/2006 | White |
| 2004/0220567 A1 | 11/2004 | Eisermann et al. | | 2006/0265068 A1 | 11/2006 | Schwab |
| 2004/0236327 A1 | 11/2004 | Paul et al. | | 2006/0265074 A1 | 11/2006 | Krishna |
| 2004/0236329 A1 | 11/2004 | Panjabi | | 2007/0010886 A1 | 1/2007 | Banick |
| 2004/0243240 A1 | 12/2004 | Beaurain et al. | | 2007/0073406 A1 | 3/2007 | Gordon et al. |
| 2004/0254643 A1 | 12/2004 | Jackson | | 2007/0213821 A1 | 9/2007 | Kwak et al. |
| 2004/0254644 A1* | 12/2004 | Taylor ........................ 623/17.13 | | 2007/0225814 A1 | 9/2007 | Atkinson |
| 2004/0267364 A1 | 12/2004 | Carli et al. | | 2007/0239279 A1 | 10/2007 | Francis |
| 2004/0267369 A1 | 12/2004 | Lyons et al. | | 2008/0027547 A1 | 1/2008 | Yu et al. |
| 2005/0010295 A1 | 1/2005 | Michelson | | 2008/0033562 A1 | 2/2008 | Krishna |
| 2005/0015146 A1 | 1/2005 | Louis et al. | | 2008/0177310 A1 | 7/2008 | Reiley |
| 2005/0015149 A1 | 1/2005 | Michelson | | 2008/0312692 A1 | 12/2008 | Brennan et al. |
| 2005/0021144 A1 | 1/2005 | Malberg et al. | | 2009/0143862 A1 | 6/2009 | Trieu |
| 2005/0027361 A1 | 2/2005 | Reiley | | 2009/0177196 A1 | 7/2009 | Zlock et al. |
| 2005/0033431 A1 | 2/2005 | Gordon et al. | | 2010/0174317 A1 | 7/2010 | Timm et al. |
| 2005/0033437 A1* | 2/2005 | Bao et al. .................... 623/17.15 | | 2010/0222819 A1 | 9/2010 | Timm et al. |
| 2005/0033439 A1 | 2/2005 | Gordon et al. | | | | |
| 2005/0060034 A1 | 3/2005 | Berry | | | | |

FOREIGN PATENT DOCUMENTS

| | | |
|---|---|---|
| FR | 2718946 | 10/1995 |
| FR | 2735351 | 12/1996 |
| FR | 2745706 | 9/1997 |
| FR | 2799949 | 4/2001 |
| RU | 2085145 | 7/1997 |
| WO | 9848739 | 11/1998 |
| WO | 0004851 | 2/2000 |
| WO | 0074606 | 12/2000 |
| WO | 0101893 | 1/2001 |
| WO | 0156513 | 8/2001 |
| WO | 0245625 | 6/2002 |
| WO | 2004019762 | 3/2004 |
| WO | 2004019828 | 3/2004 |
| WO | 2004019829 | 3/2004 |
| WO | 2004019830 | 3/2004 |
| WO | 2004024011 | 3/2004 |
| WO | 2004026188 | 4/2004 |
| WO | 2004054479 | 7/2004 |
| WO | 2006066198 | 6/2006 |

OTHER PUBLICATIONS

Claims from U.S. Appl. No. 11/050,632 to Gordon et al. entitled "Functional Spinal Units" filed on Feb. 3, 2005.

U.S. Patent and Trademark Office "Communication" for U.S. Appl. No. 11/343,933 mailed Nov. 11, 2007.

| | | |
|---|---|---|
| 2005/0107881 A1 | 5/2005 | Neville et al. |
| 2005/0124991 A1 | 6/2005 | Jahng |
| 2005/0125061 A1 | 6/2005 | Zucherman et al. |
| 2005/0131406 A1 | 6/2005 | Reiley |
| 2005/0143818 A1 | 6/2005 | Yuan et al. |
| 2005/0149020 A1 | 7/2005 | Jahng |
| 2005/0149023 A1 | 7/2005 | Ritland |
| 2005/0154461 A1 | 7/2005 | Humphreys et al. |
| 2005/0154465 A1 | 7/2005 | Hodges et al. |
| 2005/0154466 A1 | 7/2005 | Humphreys et al. |
| 2005/0159818 A1 | 7/2005 | Blain |
| 2005/0171543 A1 | 8/2005 | Timm et al. |
| 2005/0171608 A1 | 8/2005 | Peterman et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0209697 A1 | 9/2005 | Paponneau et al. |
| 2005/0209698 A1 | 9/2005 | Gordon et al. |
| 2005/0222569 A1 | 10/2005 | Panjabi |
| 2005/0228500 A1 | 10/2005 | Kim et al. |
| 2005/0245930 A1 | 11/2005 | Timm et al. |

U.S. Patent and Trademark Office "Communication" for U.S. Appl. No. 11/134,091 mailed Feb. 21, 2008.
U.S. Patent and Trademark Office "Communication" for U.S. Appl. No. 11/134,092 mailed Feb. 21, 2008.
U.S. Patent and Trademark Office "Communication" for U.S. Appl. No. 11/343,933 mailed Jul. 3, 2008.
U.S. Patent and Trademark Office "Communication" for U.S. Appl. No. 11/343,933 mailed Jun. 30, 2008.
U.S. Patent and Trademark Office "Communication" for U.S. Appl. No. 11/050,632 mailed Sep. 24, 2008.
U.S. Patent and Trademark Office "Communication" for U.S. Appl. No. 11/050,632 mailed Apr. 16, 2009.
U.S. Patent and Trademark Office "Communication" for U.S. Appl. No. 11/134,066 mailed Dec. 4, 2008.
U.S. Patent and Trademark Office "Communication" for U.S. Appl. No. 11/134,091 mailed Dec. 24, 2008.
U.S. Patent and Trademark Office "Communication" for U.S. Appl. No. 11/134,069 mailed Dec. 24, 2008.
U.S. Patent and Trademark Office "Communication" for U.S. Appl. No. 11/134,069 mailed Jun. 5, 2009.
U.S. Patent and Trademark Office "Communication" for U.S. Appl. No. 11/134,082 mailed Dec. 3, 2008.
U.S. Patent and Trademark Office "Communication" for U.S. Appl. No. 11/134,055 mailed Aug. 25, 2008.
U.S. Patent and Trademark Office "Communication" for U.S. Appl. No. 11/345,602 mailed Mar. 31, 2009.
Humphreys et al., "Biomechanics of the KENTI (TM) Total Joint Replacement", Presented at the Global Symposium on Motion Preservation Technology, May 9-13, 2006; 3 pages.
Hodges et al., "Biomechanics of the KENTI (TM) Total Joint Replacement", Presented at the Global Symposium on Motion Preservation Technology, May 9-13, 2006; 1 page.
Patel et al., "Changes in Kinematics following Single Level fusion, Single and Bi-Level Charite disc replacement in the Lumbar Spine" Presented at the Global Symposium on Motion Preservation Technology, May 9-13, 2006; 1 page.
Serhan et al. "Biomechanics of the posterior lumbar articulating elements," Neurosurg Focus 2007, 22(1):E1, 6 pages.
Khoueir et al. "Classification of posterior dynamic stabilization devices," Neurosurg Focus, 2007, 22(1):E1, 8 pages.
U. S. Patent and Trademark Office "Communication" for U.S. Appl. No. 11/371,190, mailed Oct. 11, 2007.
U. S. Patent and Trademark Office "Communication" for U.S. Appl. No. 11/371,376, mailed Nov. 29, 2007.
PCT Search Report and Written Opinion for International Application No. PCT/US2007/06395 mailed Dec. 11, 2007, 15 pages.
U. S. Patent and Trademark Office "Communication" for U.S. Appl. No. 11/371,182, mailed Jun. 9, 2008.
U. S. Patent and Trademark Office "Communication" for U.S. Appl. No. 11/371,190, mailed Apr. 17, 2008.
U. S. Patent and Trademark Office "Communication" for U.S. Appl. No. 11/371,188, mailed Mar. 17, 2009.
U. S. Patent and Trademark Office "Communication" for U.S. Appl. No. 11/371,182, mailed Oct. 11, 2007.
U. S. Patent and Trademark Office "Communication" for U.S. Appl. No. 11/371,182, mailed Jun. 9, 2008.
U. S. Patent and Trademark Office "Communication" for U.S. Appl. No. 11/371,182, mailed Dec. 12, 2008.
U. S. Patent and Trademark Office "Communication" for U.S. Appl. No. 11/371,182, mailed Mar. 25, 2009.
U. S. Patent and Trademark Office "Communication" for U.S. Appl. No. 11/371,182, mailed Apr. 24, 2009.
U. S. Patent and Trademark Office "Communication" for U.S. Appl. No. 11/371,376, mailed Apr. 20, 2009.
U. S. Patent and Trademark Office "Communication" for U.S. Appl. No. 11/371,328, mailed Mar. 17, 2009.
U. S. Patent and Trademark Office "Communication" for U.S. Appl. No. 11/371,190, mailed Aug. 11, 2008.
U. S. Patent and Trademark Office "Communication" for U.S. Appl. No. 11/655,724, mailed May 27, 2009.
U. S. Patent and Trademark Office "Communication" for U.S. Appl. No. 11/655,787, mailed May 27, 2009.
U. S. Patent and Trademark Office "Communication" for U.S. Appl. No. 11/655,737, mailed May 27, 2009.
U. S. Patent and Trademark Office "Communication" for U.S. Appl. No. 11/655,723, mailed May 27, 2009.
U. S. Patent and Trademark Office "Communication" for U.S. Appl. No. 11/655,790, mailed Jun. 4, 2009.
U. S. Patent and Trademark Office "Communication" for U.S. Appl. No. 11/371,182, mailed Jul. 21, 2009.
U. S. Patent and Trademark Office "Communication" for U.S. Appl. No. 11/134,073, mailed Jul. 22, 2009.
International Preliminary Report on Patentability for International Application No. PCT/US2008/051346 mailed Mar. 27, 2009, 23 pages.
International Search Report and Written Opinion for International Application No. PCT/US2008/051346 mailed Sep. 9, 2008, 20 pages.
U. S. Patent and Trademark Office "Communication" for U.S. Appl. No. 11/371,376, mailed Aug. 28, 2009.
U. S. Patent and Trademark Office "Communication" for U.S. Appl. No. 11/371,328, mailed Sep. 28, 2009.
U. S. Patent and Trademark Office "Communication" for U.S. Appl. No. 11/371,188, mailed Sep. 25, 2009.
U. S. Patent and Trademark Office "Communication" for U.S. Appl. No. 11/371,190, mailed Apr. 29, 2009.
U. S. Patent and Trademark Office "Communication" for U.S. Appl. No. 11/371,182, mailed Oct. 14, 2009.
U. S. Patent and Trademark Office "Communication" for U.S. Appl. No. 11/371,190, mailed Nov. 7, 2008.
U. S. Patent and Trademark Office "Communication" for U.S. Appl. No. 11/371,190, mailed Oct. 29, 2009.
U. S. Patent and Trademark Office "Communication" for U.S. Appl. No. 11/371,170, mailed Nov. 4, 2009.
U. S. Patent and Trademark Office "Communication" for U.S. Appl. No. 11/343,933 mailed Nov. 19, 2007.
U. S. Patent and Trademark Office "Communication" for U.S. Appl. No. 11/371,376, mailed Nov. 4, 2009.
U. S. Patent and Trademark Office "Communication" for U.S. Appl. No. 11/345,602, mailed Oct. 13, 2009.
PCT Search Report and Written Opinion for PCT/US2004/025090 mailed on Apr. 11, 2005 (8 pages).
U.S. Patent and Trademark Office "Communication" for U.S. Appl. No. 11/343,933 mailed Nov. 19, 2007.
U. S. Patent and Trademark Office "Communication" for U.S. Appl. No. 11/134,073, mailed Jul. 22, 2009.
U. S. Patent and Trademark Office "Communication" for U.S. Appl. No. 11/134,079, mailed Aug. 14, 2009.
U. S. Patent and Trademark Office "Communication" for U.S. Appl. No. 11/134,082, mailed Aug. 14, 2009.
U. S. Patent and Trademark Office "Communication" for U.S. Appl. No. 11/134,067, mailed Aug. 14, 2009.
U. S. Patent and Trademark Office "Communication" for U.S. Appl. No. 11/050,632, mailed Aug. 25, 2009.
U. S. Patent and Trademark Office "Communication" for U.S. Appl. No. 11/134,066, mailed Sep. 9, 2009.
U. S. Patent and Trademark Office "Communication" for U.S. Appl. No. 11/655,724, mailed Nov. 23, 2009.
U. S. Patent and Trademark Office "Communication" for U.S. Appl. No. 11/655,787, mailed Nov. 23, 2009.
U. S. Patent and Trademark Office "Communication" for U.S. Appl. No. 11/655,737, mailed Nov. 23, 2009.
U. S. Patent and Trademark Office "Communication" for U.S. Appl. No. 11/655,723, mailed Nov. 24, 2009.
U. S. Patent and Trademark Office "Communication" for U.S. Appl. No. 11/371,328, mailed Dec. 30, 2009.
U. S. Patent and Trademark Office "Communication" for U.S. Appl. No. 11/134,069, mailed Dec. 30, 2009.
U. S. Patent and Trademark Office "Communication" for U.S. Appl. No. 11/134,055, mailed Jan. 19, 2010.
U. S. Patent and Trademark Office "Communication" for U.S. Appl. No. 11/134,073, mailed Jan. 27, 2010.
U. S. Patent and Trademark Office "Communication" for U.S. Appl. No. 11/134,091, mailed Jan. 26, 2010.

U. S. Patent and Trademark Office "Communication" for U.S. Appl. No. 11/371,170, mailed May 4, 2010.
U. S. Patent and Trademark Office "Communication" for U.S. Appl. No. 11/371,376, mailed May 26, 2010.
U. S. Patent and Trademark Office "Communication" for U.S. Appl. No. 11/526,849, mailed Jun. 1, 2010.
U. S. Patent and Trademark Office "Communication" for U.S. Appl. No. 11/655,790, mailed Mar. 15, 2010.
U. S. Patent and Trademark Office "Communication" for U.S. Appl. No. 11/134,069, mailed Apr. 19, 2010.
U. S. Patent and Trademark Office "Communication" for U.S. Appl. No. 11/371,188, mailed Apr. 28, 2010.
U. S. Patent and Trademark Office "Communication" for U.S. Appl. No. 11/050,632, mailed Mar. 2, 2010.
U. S. Patent and Trademark Office "Communication" for U.S. Appl. No. 11/371,190, mailed Feb. 26, 2010.
U. S. Patent and Trademark Office "Communication" for U.S. Appl. No. 11/134,082, mailed Mar. 12, 2010.
U. S. Patent and Trademark Office "Communication" for U.S. Appl. No. 11/134,082, mailed May 25, 2010.
U. S. Patent and Trademark Office "Communication" for U.S. Appl. No. 10/777,411, mailed Jun. 9, 2010.
U. S. Patent and Trademark Office "Communication" for U.S. Appl. No. 11/371,328, mailed Jun. 17, 2010.
U. S. Patent and Trademark Office "Communication" for U.S. Appl. No. 11/371,188, mailed Jun. 15, 2010.
U. S. Patent and Trademark Office "Communication" for U.S. Appl. No. 11/371,182, mailed Jun. 8, 2010.
U. S. Patent and Trademark Office "Communication" for U.S. Appl. No. 11/371,170, mailed May 4, 2010.
U. S. Patent and Trademark Office "Communication" for U.S. Appl. No. 11/371,182, mailed Feb. 8, 2010.
U. S. Patent and Trademark Office "Communication" for U.S. Appl. No. 11/134,066, mailed Feb. 18, 2010.
U. S. Patent and Trademark Office "Communication" for U.S. Appl. No. 11/374,079, mailed Feb. 19, 2010.
U. S. Patent and Trademark Office "Communication" for U.S. Appl. No. 11/134,067, mailed Feb. 18, 2010.
U. S. Patent and Trademark Office "Communication" for U.S. Appl. No. 11/371,376, mailed Jul. 29, 2010.
U. S. Patent and Trademark Office "Communication" for U.S. Appl. No. 11/371,190, mailed Aug. 11, 2010.
U. S. Patent and Trademark Office "Communication" for U.S. Appl. No. 11/134,091, mailed Aug. 4, 2010.
U. S. Patent and Trademark Office "Communication" for U.S. Appl. No. 11/975,916, mailed Aug. 4, 2010.
U. S. Patent and Trademark Office "Communication" for U.S. Appl. No. 11/975,917, mailed Aug. 17, 2010.
U. S. Patent and Trademark Office "Communication" for U.S. Appl. No. 11/975,919, mailed Aug. 19, 2010.
U. S. Patent and Trademark Office "Communication" for U.S. Appl. No. 11/371,182, mailed Aug. 25, 2010.
U. S. Patent and Trademark Office "Communication" for U.S. Appl. No. 11/371,188, mailed Sep. 1, 2010.
U. S. Patent and Trademark Office "Communication" for U.S. Appl. No. 10/777,411, mailed Oct. 15, 2010.

* cited by examiner

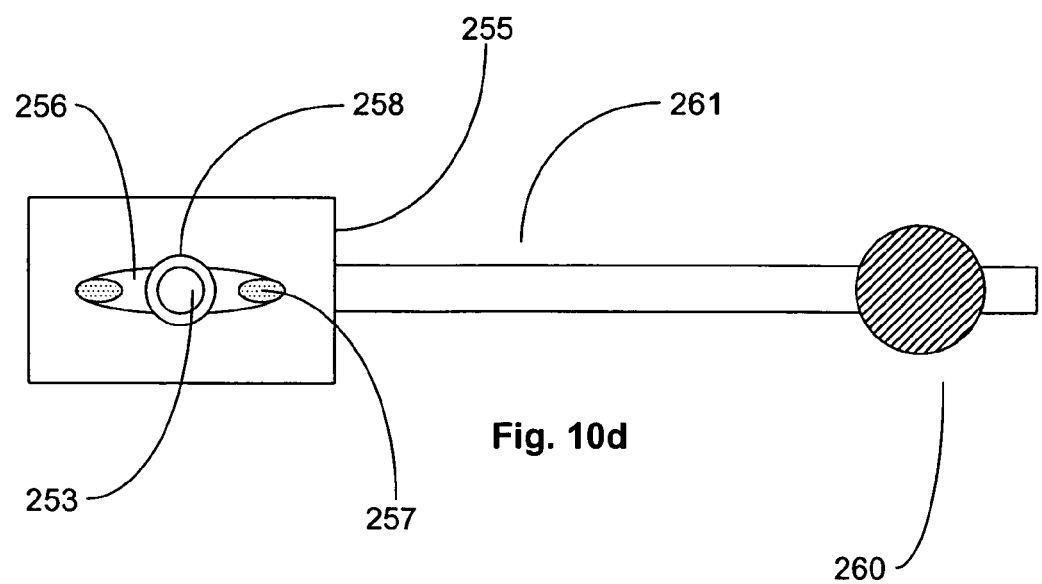
Fig. 10d
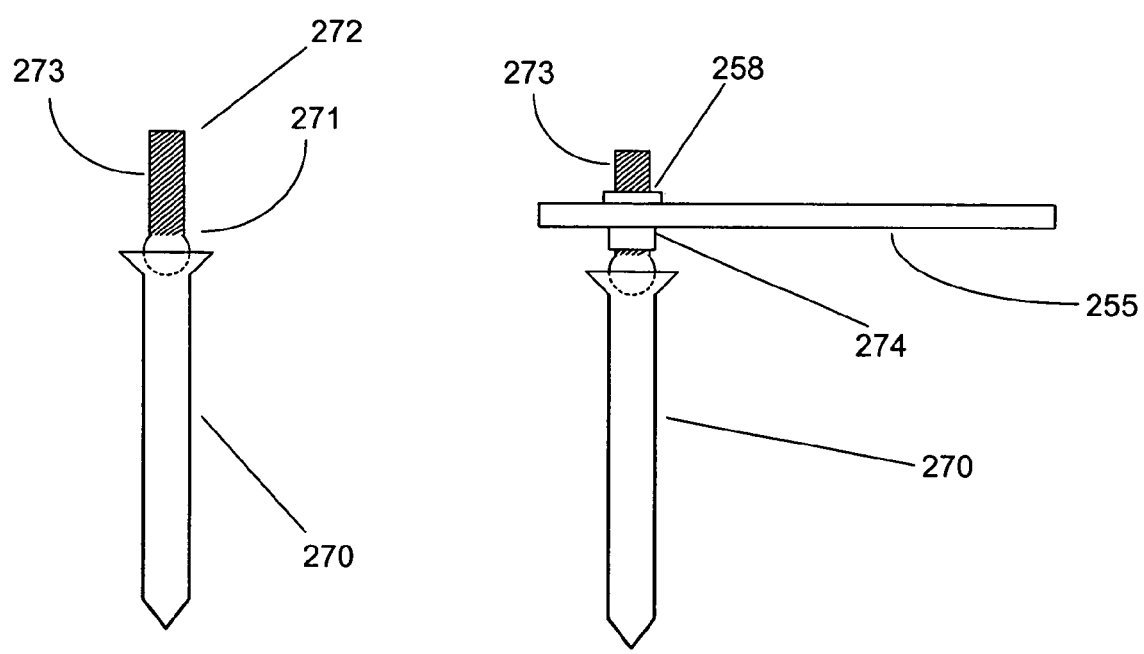
Fig. 10e
Fig. 10f

ARTIFICIAL SPINAL UNIT ASSEMBLIES

This application is a continuation-in-part of U.S. patent application Ser. No. 10/634,950, filed Aug. 5, 2003 now U.S. Pat. No. 7,204,853.

STATEMENT REGARDING FEDERALLY SPONSORED RESEARCH OR DEVELOPMENT

Not applicable

FIELD OF THE INVENTION

The present invention generally relates to functional spinal implant assemblies for insertion into the intervertebral space between adjacent vertebral bones and reconstruction of the posterior elements to provide stability, flexibility and proper biomechanical motion. More specifically, the present invention relates to artificial functional spinal units comprising an expandable artificial intervertebral implant that can be inserted via a posterior surgical approach and used in conjunction with one or more artificial facet joints to provide a more anatomically correct range of motion. While a posterior surgical approach is preferred, the invention described herein may also be used in conjunction with an anterior surgical approach.

BACKGROUND OF THE INVENTION

The human spine is a complex mechanical structure composed of alternating bony vertebrae and fibrocartilaginous discs that are connected by strong ligaments and supported by musculature that extends from the skull to the pelvis and provides axial support to the body. The intervertebral discs primarily serve as a mechanical cushion between adjacent vertebral segments of the spinal column and generally comprise three basic components: the nucleus pulposus, the anulus fibrosis, and two vertebral end plates. The end plates are made of thin cartilage overlying a thin layer of hard cortical bone that attaches to the spongy, cancellous bone of the vertebral body. The anulus fibrosis forms the disc's perimeter and is a tough outer ring that binds adjacent vertebrae together. The vertebrae generally comprise a vertebral foramen bounded by the anterior vertebral body and the neural arch, which consists of two pedicles and two laminae that are united posteriorly. The spinous and transverse processes protrude from the neural arch. The superior and inferior articular facets lie at the root of the transverse process. The term "functional spinal unit" ("FSU") refers to the entire motion segment: the anterior disc and the posterior facet joints, along with the supporting ligaments and connective tissues.

The spine as a whole is a highly flexible structure capable of a high degree of curvature and twist in nearly every direction. However, genetic or developmental irregularities, trauma, chronic stress, and degenerative wear can result in spinal pathologies for which surgical intervention maybe necessary.

It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the anulus to buckle in areas where the laminated plies are loosely bonded. As the overlapping laminated plies of the anulus begin to buckle and separate, either circumferential or radial anular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. U.S. Pat. No. 4,863,477 discloses a resilient spinal disc prosthesis intended to replace the resiliency of a natural human spinal disc. U.S. Pat. No. 5,192,326 teaches a prosthetic nucleus for replacing just the nucleus portion of a human spinal disc.

In other cases it is desired to fuse the adjacent vertebrae together after removal of the disc, sometimes referred to as "intervertebral fusion" or "interbody fusion."

Many techniques and instruments have been devised to perform intervertebral fusion. There is common agreement that the strongest intervertebral fusion is the interbody (between the lumbar bodies) fusion, which may be augmented by a posterior or facet fusion. In cases of intervertebral fusion, either structural bone or an interbody fusion cage filled with morselized bone is placed centrally within the space where the spinal disc once resided. Multiple cages or bony grafts may be used within that space.

Such practices are characterized by certain disadvantages, most important of which is the actual morbidity of the procedure itself. Placement of rigid cages or structural grafts in the interbody space either requires an anterior surgical approach, which carries certain unavoidable risks to the viscous structures overlying the spine (intestines, major blood vessels, and the ureter), or they may be accomplished from a posterior surgical approach, thereby requiring significant traction on the overlying nerve roots. The interval between the exiting and traversing nerve roots is limited to a few millimeters and does not allow for safe passage of large intervertebral devices, as may be accomplished from the anterior approach. Alternatively, the anterior approach does not allow for inspection of the nerve roots, is not suitable alone for cases in which the posterior elements are not competent, and most importantly, the anterior approach is associated with very high morbidity and risk where there has been previous anterior surgery.

Another significant drawback to fusion surgery in general is that adjacent vertebral segments show accelerated deterioration after a successful fusion has been performed at any level. The spine is by definition stiffer after the fusion procedure, and the natural body mechanics place increased stress on levels proximal to the fused segment. Other drawbacks include the possibility of "flat back syndrome" in which there is a disruption in the natural curvature of the spine. The vertebrae in the lower lumbar region of the spine reside in an arch referred as having a sagittal alignment. The sagittal alignment is compromised when adjacent vertebral bodies that were once angled toward each other on their posterior side become fused in a different, less angled orientation relative to one another. Finally, there is always the risk that the fusion attempt may fail, leading to pseudoarthrosis, an often painful condition that may lead to device failure and further surgery.

Conventional interbody fusion cages generally comprise a tubular metal body having an external surface threading. They are inserted transverse to the axis of the spine, into preformed cylindrical holes at the junction of adjacent vertebral bodies. Two cages are generally inserted side by side with the external threading tapping into the lower surface of the vertebral bone above, and the upper surface of the vertebral bone below. The cages include holes through which the adjacent bones are to grow. Additional materials, for example autogenous bone graft materials, maybe inserted into the hollow interior of the cage to incite or accelerate the growth of the bone into the cage. End caps are often utilized to hold the bone graft material within the cage.

These cages of the prior art have enjoyed medical success in promoting fusion and grossly approximating proper disc height. As previously discussed, however, cages that would be placed from the safer posterior route would be limited in size by the interval between the nerve roots. It would therefore, be a considerable advance in the art to provide a fusion implant assembly which could be expanded from within the intervertebral space, thereby minimizing potential trauma to the nerve roots and yet still providing the ability to restore disc space height.

Ultimately though, it is important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. Thus, it would be an even greater advance in the art to provide an implant assembly that does not promote fusion, but instead closely mimics the biomechanical action of the natural disc cartilage, thereby permitting continued normal motion and stress distribution.

SUMMARY OF THE INVENTION

Accordingly, an artificial functional spinal unit (FSU) is provided comprising, generally, an expandable artificial intervertebral implant that can be placed via a posterior surgical approach and used in conjunction with one or more artificial facet joints to provide an anatomically correct range of motion. Expandable artificial intervertebral implants in both lordotic and non-lordotic designs are disclosed, as well as lordotic and non-lordotic expandable cages for both PLIF (posterior lumber interbody fusion) and TLIF (transforaminal lumbar interbody fusion) procedures. The expandable implants may have various shapes, such as round, square, rectangular, trapezoidal, banana-shaped, kidney-shaped, or other similar shapes. By virtue of their posteriorly implanted approach, the disclosed artificial FSU's allow for posterior decompression of the neural elements, reconstruction of all or part of the natural functional spinal unit, restoration and maintenance of lordosis, maintenance of motion, and restoration and maintenance of disc space height.

The posterior implantation of an interbody device provides critical benefits over other anterior implanted devices. Placement of posterior devices that maintain mobility in the spine have been limited due to the relatively small opening that can be afforded posteriorly between the exiting and transversing nerve roots. Additionally, placement of posterior interbody devices requires the removal of one or both facet joints, further destabilizing the spine. Thus conventional posteriorly placed interbody devices have been generally limited to interbody fusion devices.

Since a properly functioning natural FSU relies on intact posterior elements (facet joints) and since it is necessary to remove these elements to place a posterior interbody device, a two-step procedure is disclosed that allows for placement of an expandable intervertebral implant and replacement of one or both facets that are necessarily removed during the surgical procedure. The expansile nature of the disclosed devices allow for restoration of disc height once inside the vertebral interspace. The expandable devices are collapsed prior to placement and then expanded once properly inserted in the intervertebral space. During the process of expansion, the endplates of the natural intervertebral disc, which essentially remain intact after removal or partial removal of the remaining natural disc elements, are compressed against the device, which thereby facilitates bony end growth onto the surface of the artificial implant. Once the interbody device is in place and expanded, the posterior element is reconstructed with the disclosed pedicle screw and rod system, which can also be used to distract the disk space while inserting the artificial implant. Once the interbody device is in place and expanded, the posterior element is further compressed, again promoting bony end growth into the artificial implant. This posterior compression allows for anterior flexion but replaces the limiting element of the facet and interspinous ligament and thereby limits flexion to some degree, and in doing so maintains stability for the anteriorly located interbody device.

The posterior approach avoids the potential risks and morbidity of the anterior approach, which requires mobilization of the vascular structures, the ureter, and exposes the bowels to risk. Also, the anterior approach does not offer the surgeon an opportunity to view the posterior neural elements and thereby does not afford an opportunity for decompression of those elements. Once an anterior exposure had been utilized a revision procedure is quite risky and carries significant morbidity.

While the posterior surgical approach is preferred, there may be circumstances that prevent posterior placement. If an anterior approach must be performed, the disclosed devices may be inserted anteriorly without affecting functionality.

The artificial FSU generally comprises an expandable intervertebral implant and one or more artificial facet joints. The expandable intervertebral implant generally comprises a pair of spaced apart plate members, each with a vertebral body contact surface. The general shape of the plate members may be round, square, rectangular, trapezoidal, banana shaped, kidney shaped, or some other similar shape, depending on the desired vertebral implantation site. Because the artificial intervertebral implant is to be positioned between the facing surfaces of adjacent vertebral bodies, the plate members are arranged in a substantially parallel planar alignment (or slightly offset relative to one another in accordance with proper lordotic angulation) with the vertebral body contact surfaces facing away from one another. The plate members are to mate with the vertebral bodies so as to not rotate relative thereto, but rather to permit the spinal segments to axially compress and bend relative to one another in manners that mimic the natural motion of the spinal segment. This natural motion is permitted by the performance of an expandable joint insert, which is disposed between the plate members. The securing of the plate members to the vertebral bone is achieved through the use of a osteoconductive scaffolding machined into the exterior surface of each plate member. Alternatively, a mesh of osteoconductive surface may be secured to the exterior surface of the plate members by methods known in the art. The osteoconductive scaffolding provides a surface through which bone may ultimately grow. If an osteoconductive mesh is employed, it may be constructed of any biocompatible material, both metal and non-metal. Each plate member may also comprise a porous coating (which may be a sprayed deposition layer, or an adhesive applied beaded metal layer, or other suitable porous coatings known in the art, i.e. hydroxy appetite). The porous coating permits the long-term ingrowth of vertebral bone into the plate member, thus permanently securing the prosthesis within the intervertebral space.

In more detail, the expandable artificial implant of the present invention comprises four parts: an upper body, a lower body, an expandable joint insert that fits into the lower body, and an expansion device, which may be an expansion plate, screw, or other similar device. The upper body generally comprises a substantially concave inferior surface and a substantially planar superior surface. The substantially planar superior surface of the upper body may have some degree of convexity to promote the joining of the upper body to the intact endplates of the natural intervertebral disc upon compression. The lower body generally comprises a recessed channel, having a rectangular cross section, which extends along the superior surface of the lower body in the medial-lateral direction and substantially conforms to the shape of the upper and lower bodies. The lower body further comprises a substantially planar inferior surface that may have some degree of convexity to promote the joining of the lower body to the intact endplates of the natural intervertebral disc upon compression. The expandable joint insert resides within the channel on the superior surface of the lower body. The expandable joint insert has a generally flat inferior surface and a substantially convex superior surface that articulates with the substantially concave inferior surface of the upper body. Prior to expansion of the artificial implant, the generally flat inferior surface of the expandable joint insert rests on the bottom surface of the channel. The expandable joint insert is raised above the bottom of the channel by means of an expansion screw, an expansion plate, or other similar device, that is inserted through an expansion hole or slot. The expansion hole or slot is disposed through the wall of the lower body formed by the channel. The expansion hole or slot gives access to the lower surface of the channel and is positioned such that the expansion device can be inserted into the expansion hole or slot via a posterior surgical approach. As the expansion device is inserted through the expansion slot, into the channel, and under the expandable joint insert, the expandable joint insert is raised above the floor of the channel and lifts the upper body above the lower body to the desired disc height. The distance from the inferior surface of the lower body and the superior surface of the upper body should be equal to the ideal distraction height of the disk space. As the artificial implant is flexed and extended, the convex superior surface of the expandable joint insert articulates with the concave inferior surface of the upper body.

After the insertion and expansion of the expandable intervertebral implant, the posterior facet joints may be reconstructed by employing the disclosed artificial facet joints. One embodiment of the artificial facet joint generally comprises a lower and upper multi-axial pedicle screw joined by a rod bridging the vertebral bodies above and below the artificial implant. The rod comprises a washer-type head at its lower (caudad) end. The rod fits into the heads of the pedicle screws and a top loaded set screw is placed in the pedicle screw heads. The disclosed pedicle screw system may employ different types of pedicle screws so that the top loaded set screw may or may not lock down on the rod depending on surgeon preference. If a non-locking pedicle screw is used the caudad end remains fully multi-axial. The upper (cephalad) end of the rod is held within the head of the upper pedicle screw with a set screw which locks down on the rod and eliminates any rod movement at the cephalad end, which by nature has limited multi-axial function. In an alternative embodiment of an artificial facet joint, the rod may comprise washer-type heads on both ends (caudad and cephalad) so that both pedicle screws can be of the non-locking variety. In the event of a two level surgical procedure, three pedicle screws would be employed with a single rod, which would have washer-type heads at both ends. The middle pedicle screw would be a locking-type and the upper most and lower most pedicle screws would be of the non-locking variety.

In addition, another embodiment of the artificial facet joint is disclosed that generally comprises two locked pedicle screws joined by a rod having a ball and socket joint centrally located on the rod between the two pedicle screws. The locking of the pedicle screws prevents the screw head from swiveling, but allows rotation and translation of the rod.

While conventional locking type pedicle screws may be employed, a novel locking type pedicle screw is also disclosed. Locking type pedicle screws comprise a set screw located in the pedicle screw head, which applies force to the retaining rod as it is tightened. One the set screw is tightened, rotational and translational movement of the rod within the head of the pedicle screw is prohibited. In addition, the multi-axial movement of the pedicle screw head is also prohibited making the entire assembly a fixed structure. By employing the rod holding device described in detail below, the set screw can be tightened and the multi-axial movement of the pedicle screw head can be prohibited without limiting the translational and rotational movement of the retaining rod. The rod holding device generally comprises a solid insert fitting within the pedicle screw head with a hole in which the retaining rod is slidingly positioned. As the set screw is tightened, force is applied to the rod holding device and transferred to the bottom of the pedicle screw head without applying force to the retaining rod. This allows fixation of the pedicle screw head without limiting movement of the retaining rod.

In another preferred embodiment, the artificial facet joint generally comprises an upper and lower pedicle screw having post-type heads. Rather than the previously described rod, a retaining plate is employed. Elongated holes are defined through the retaining plate, which are positioned upon the post-type heads of the pedicle screws. The post-type heads are allowed to move within the elongated holes, providing limited range of motion. Employing cushioning pads made of rubber or similar biocompatible material may dampen the movement of the plate. The post-type heads may also comprise threaded or lockable caps to prevent dislocation of the plate from the post-type heads.

In instances where a fusion procedure is unavoidable, a PLIF and TLIF cages are disclosed that utilize the expansion principal of the functional artificial intervertebral implant. One embodiment of the PLIF and TLIF cages generally comprises three parts: An external body, an internal body, and an expansion device. The external and internal bodies will have substantially the same shape and will be shaped accordingly to the procedures for which they will be used, more specifically, a rectangular cage is preferred for a PLIF procedure and round or banana shaped cage is preferred for the TLIF procedure. Both the external and internal bodies comprise a mesh structure in which an osteoconductive substance can be placed (i.e. morsilized autograph or an osteobiologic substitute). The external body of the cage contains an internal void space that houses the internal body. The external body further comprises an expansion window on its superior surface through which the internal body is raised upon expansion of the cage. The internal body comprises a planar plate member that is slightly larger than the expansion window in the superior surface of the external body such that when the cage is expanded the planar plate member secures itself against the interior side of the expansion window, thereby interlocking the external and internal bodies and eliminating mobility between the two bodies. Similar to the functional expandable implant, an expansion device is placed through an expansion slot. The expansion device lifts the internal body relative to the external body, interlocking the planar plate member of the internal body against the interior of the expansion window, and pushing the mesh structure of the internal body through the expansion window and above the superior surface of the external body. Varying the height of the expansion device and the dimensions of the external and internal bodies allows for various distraction heights to regain disc space. As with the functional intervertebral implant, the PLIF and TLIF cages may take the form of either an expandable lordotic cage or a non-lordotic cage.

In another embodiment of the PLIF and TLIF cage, a joint insert is employed that is similar to that used in the functional implant. This embodiment generally comprises four parts: an upper body, a lower body, an expandable joint insert that fits into the lower body, and an expansion screw or other similar device. The upper body generally comprises a substantially planar superior surface and one or more angled projections extending downward from the upper body's inferior surface. The substantially planar superior surface of the upper body may have some degree of convexity to promote the joining of the upper body to the intact endplates of the natural intervertebral disc upon compression. The lower body generally comprises a recessed channel, preferably having a rectangular cross-section, which extends along the superior surface of the lower body in the medial-lateral direction. The lower body further comprises a substantially planar inferior surface that may have some degree of convexity to promote the joining of the lower body to the intact endplates of the natural intervertebral disc upon compression. The expandable joint insert resides within the channel on the superior surface of the lower body. The expandable joint insert has a generally flat inferior surface and one or more angled projections extending upward from the superior surface of the joint insert that are in communication with the angled projections extending downward from the inferior surface of the upper body. Expansion is accomplished by utilizing as expansion screw or other similar device through an expansion hole disposed through the lower body. Insertion of the expansion screw forces the one or more angled projections of the expansion joint insert to articulate against the one or more angled projections of the upper body causing the upper body to lift above the lower body. The maximum expansion height may be limited by employing one or more retaining pegs. The retaining pegs also prohibit dislocation and rotation of the upper body relative to the lower body.

The shapes and sizes of all of the devices disclosed herein are dependent upon the surgical approach employed to insert the device and the position in the spine in which it is placed. Generally, they will range from about 6 to about 11 millimeters in height for cervical devices and about 10 to about 18 millimeters in height for lumbar devices. However some deviation from these ranges may occur from patient to patient. Round devices will preferably range from about 14 to about 26 millimeters in diameter. Square devices will preferably range from about 14×14 to about 26×26 millimeters. Rectangular and trapezoidal devices will preferably range from about 12 millimeters along its shortest side and to about 30 millimeters along its longest side.

BRIEF DESCRIPTION OF THE DRAWINGS

FIG. 3b is a side cross-sectional view of the banana-shaped, expandable intervertebral implant shown in FIG. 3a.

FIGS. 10d-10f illustrate a pedicle screw having a post-type head.

PREFERRED EMBODIMENTS OF THE INVENTION

In the following detailed description of the preferred embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention.

Figure 1:
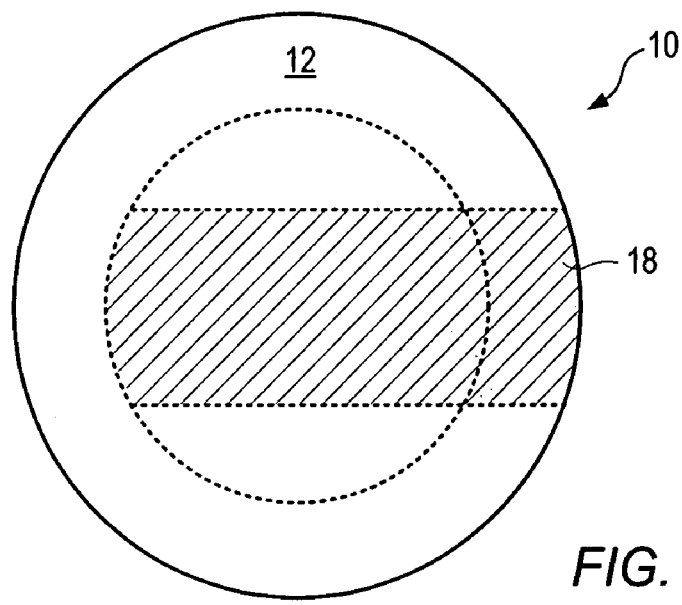
FIG. 1 is a top view of a round, expandable intervertebral implant of the present invention.
Figure 2:
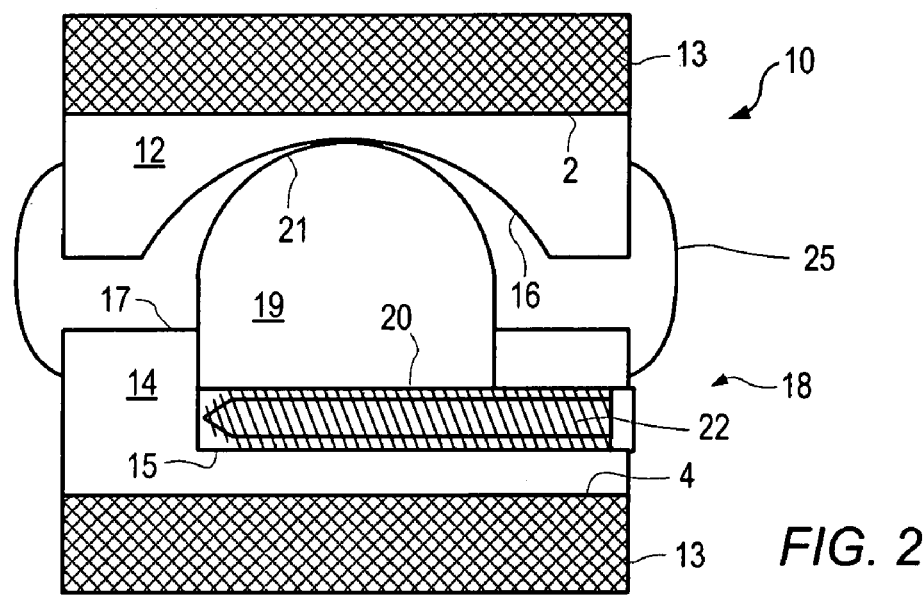
FIG. 2 is a side cross-sectional view of the round, expandable intervertebral implant shown in FIG. 1.

FIGS. 1 and 2 show a round, expandable artificial intervertebral implant designated generally at 10. The device is implemented through a posterior surgical approach by making an incision in the anulus connecting adjacent vertebral bodies after removing one or more facet joints. The natural spinal disc is removed from the incision after which the expandable artificial intervertebral implant is placed through the incision into position between the vertebral bodies. The implant is preferably made of a biocompatible metal having a non-porous quality and a smooth finish, however, it may also be constructed of ceramic or any other suitable inert material.

The expandable artificial intervertebral implant 10 generally comprises an upper body 12 and a lower body 14 in a substantially parallel planar configuration. The superior surface 2 of the upper body 12 and the inferior surface 4 of the lower body 14 comprise a machined osteoconductive scaffolding 13 through which the bone may ultimately grow. Osteoconductive scaffolding 13 may also include spines or barbs that project into and secure against the bony endplates of the adjacent bony vertebral bodies upon expansion of the joint and minimize the possibility of sublaxation and/or dislocation. The upper body 12 has a substantially concave inferior surface 16. The lower body 14 has a channel 15 in superior surface 17. Channel 15 preferably has a rectangular cross-section that extends along the lower body 14 in the medial-lateral direction and substantially conforms to the shape of the upper 12 and lower 14 bodies. An expandable joint insert 19 resides within the channel 15 on the lower body. The expandable joint insert 19 has a generally flat inferior surface 20 and a substantially convex superior surface 21 that articulates with the substantially concave inferior surface 16 of the upper body 12. The expandable joint insert 19 is lifted from the bottom of channel 15 by means of an expansion screw 22, or other device, that is inserted between the generally flat inferior surface 20 of the expandable joint insert 19 and the bottom of the channel 15 extending along the lower body 14 through an expansion slot 18. A void space is created between the expandable joint insert 19 and the floor of the channel 15 in cross sections not including the expansion device. A securing means, such as the cables 25, may be employed to ensure the upper body 12 and the lower body 14 remain intact during flexion and extension of the FSU. Alternative means for securing the upper body 12 and lower body 14 may also be employed, such as retaining pegs, torsion springs, or similar devices.

Figure 3A:
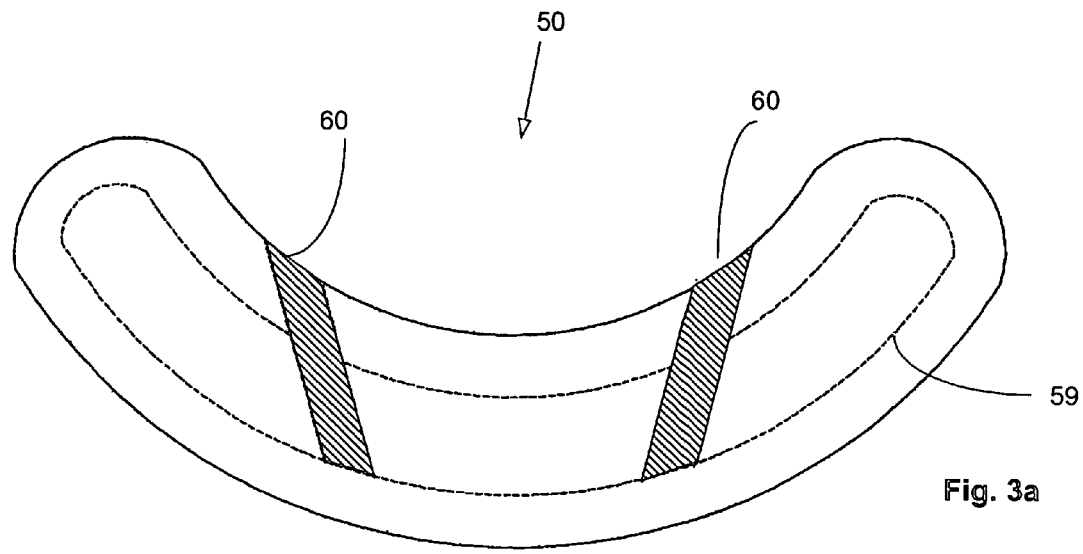
FIG. 3a is a top view of a banana-shaped, expandable intervertebral implant of the present invention.
Figure 3B:
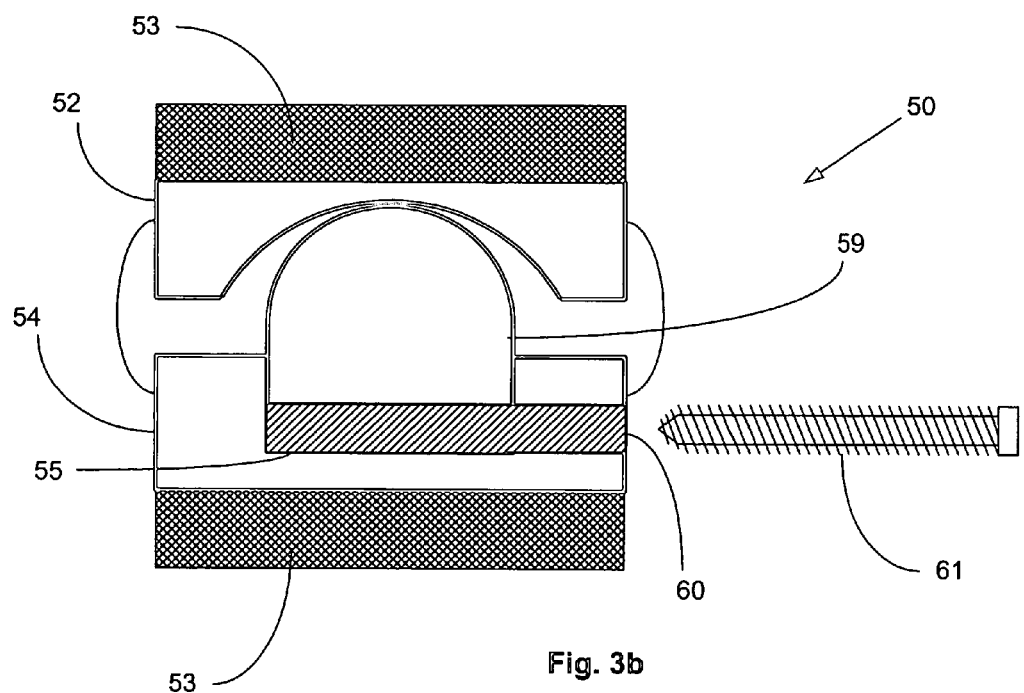

FIGS. 3a and 3b show a banana-shaped expandable artificial intervertebral implant 50. As with the round implant 10 shown in FIG. 1, the banana-shaped implant also comprises an upper body 52 and a lower body 54 in a substantially planar configuration, each having an external osteoconductive scaffolding 53. Note that the channel 55 and the expandable joint insert 59, which is disposed within the channel 55, may substantially conform to the shape of the upper 52 and lower 54 bodies. Alternatively, expandable joint insert 59 may have a different shape, such as oval or round, as compared to the shape of the upper 52 and lower 54 bodies. Whereas the round expandable implant may comprise a single expansion device, the banana-shaped implant may contain one or more expansion devices 61 that are inserted into expansion slots 60. Otherwise, the cross-section of the banana-shaped implant is substantially similar to FIG. 2.

Figure 4A:
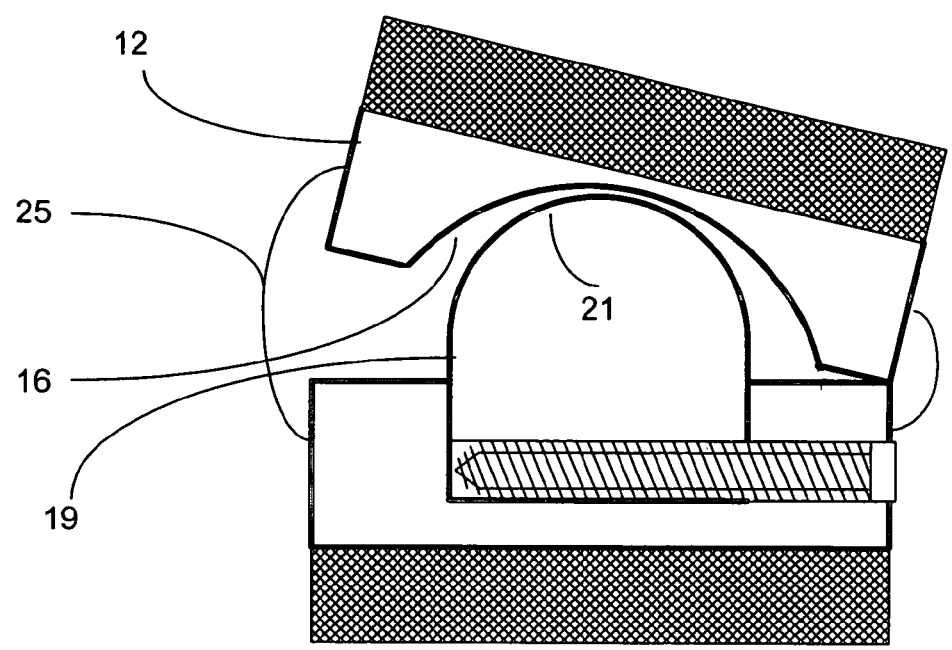
FIG. 4a is a cross-sectional illustration of an expandable intervertebral implant in compression.
Figure 4B:
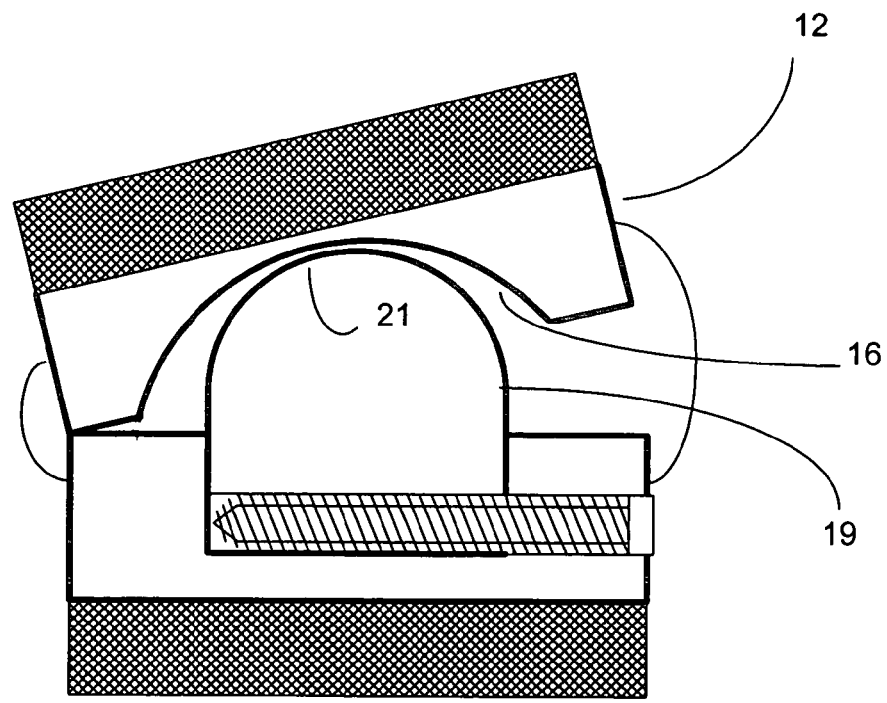
FIG. 4b is a cross-sectional illustration of an expandable intervertebral implant in flexion.

Turning to FIGS. 4a and 4b, an expandable artificial intervertebral implant is shown in flexion and extension, respectively. The concave inferior surface of 16 of upper body 12 articulates with the convex superior surface 21 of expandable joint insert 19. As stated above, securing means 25 may be employed to prevent dislocation of the implant.

Figure 5A:
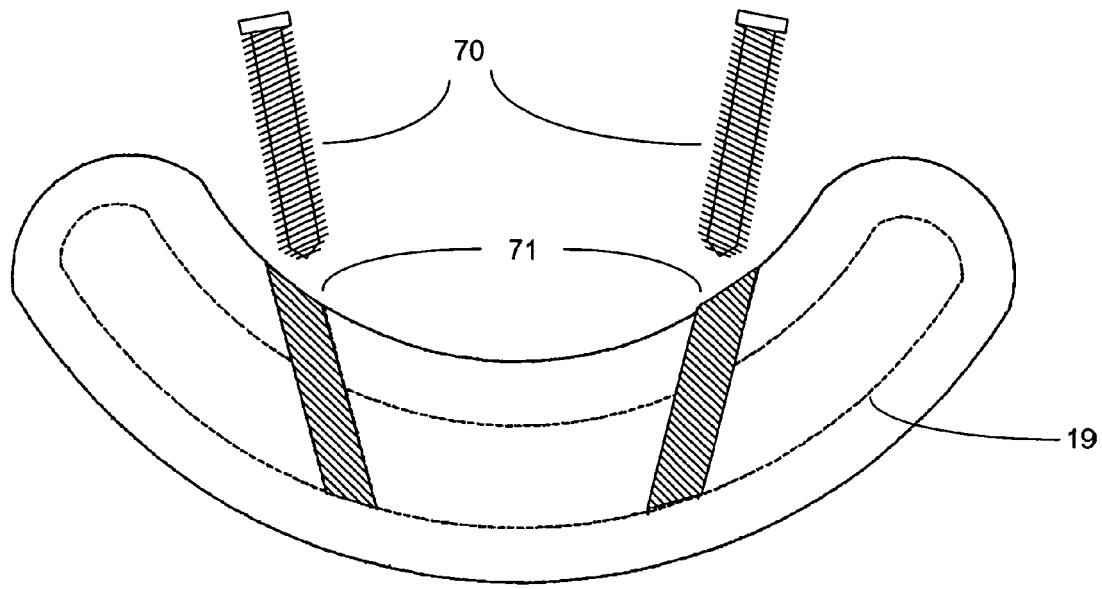
FIG. 5a is a top view of a banana-shaped, expandable intervertebral implant, illustrating the insertion of expansion screws to expand the joint.
Figure 5B:
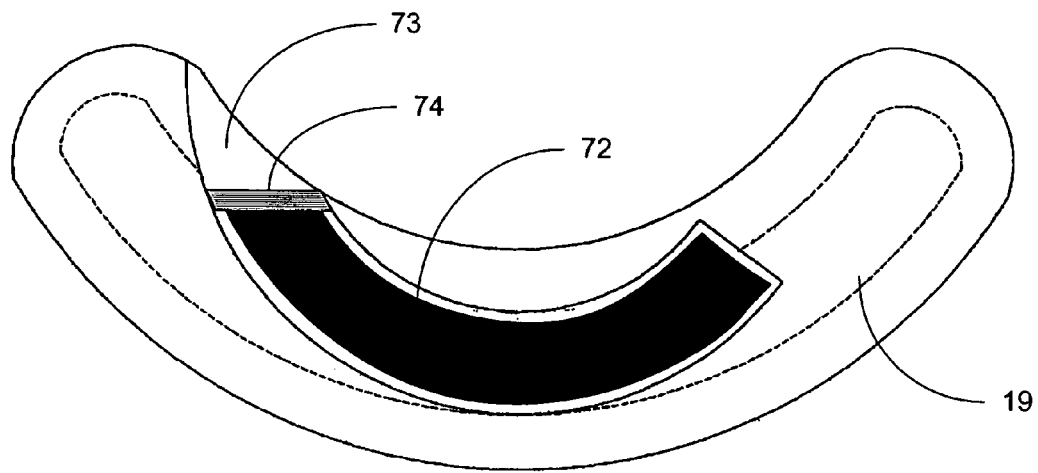
FIG. 5b is a top view of a banana-shaped, expandable intervertebral implant, illustrating the insertion of a non-threaded expansion device to expand the joint.

FIGS. 5a and 5b illustrate the insertion of expansion devices into a banana-shaped implant. The artificial intervertebral implant 50 in Figure 5a employs expansion screws 70 to expand joint insert 19. One or more expansion screws 70 may be inserted through one or more threaded expansion slots 71. Alternatively, as shown in FIG. 5b, artificial implant 55 may employ a non-threaded expansion device 72 inserted through a non-threaded expansion slot 73 to accomplish the expansion of joint insert 19. The non-threaded expansion slot 73 preferably has an arcuate shape to facilitate insertion after the artificial disc prosthesis has been properly placed within the intervertebral space. The non-threaded expansion device 72 has substantially the same shape as expansion slot 73. A threaded end cap 74 may be employed to retain the expansion device 72 inside the expansion slot 73.

Figure 5C:
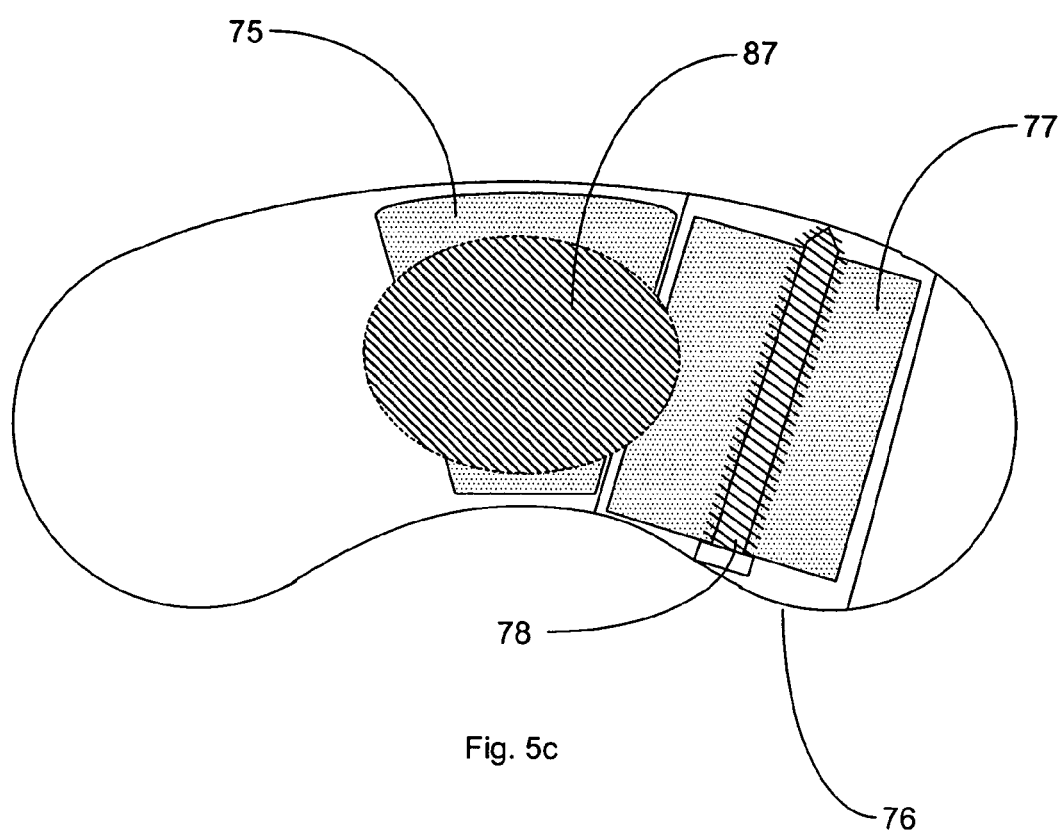
FIG. 5c is a top view of a banana-shaped, expandable intervertebral implant with a posteriorly positioned expansion window.

FIG. 5c illustrates an alternative means for posteriorly securing an expansion device. Expansion plate 75 is inserted posteriorly into expansion window 76 and slidingly engages the joint insert in the medial-lateral direction. After expansion, stop block 77, which substantially fills expansion window 76 is secured in place with screw 78 or similar device.

Figure 6A:
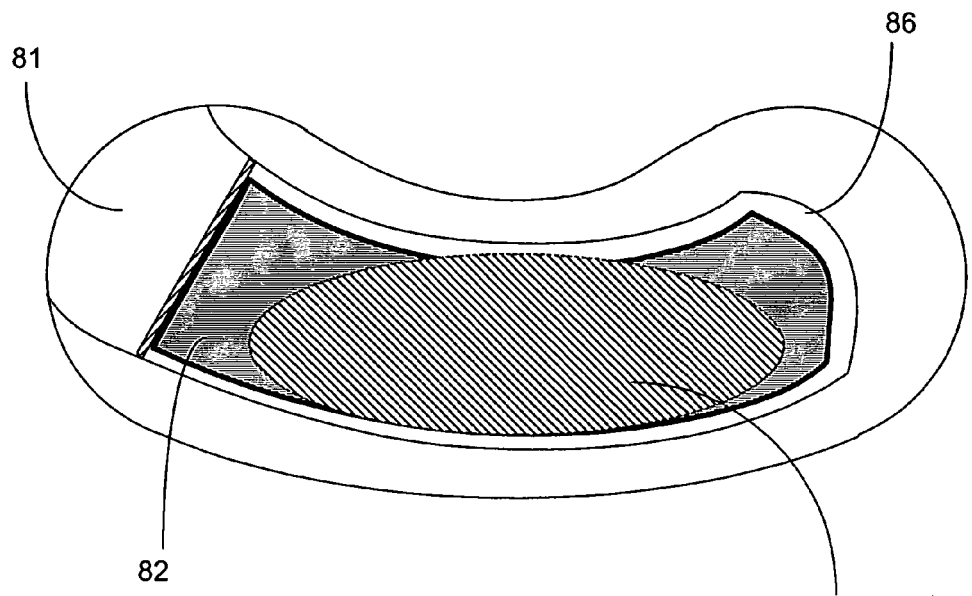
FIG. 6a is a top view of a banana-shaped, expandable intervertebral implant, illustrating the insertion of an expansion plate to expand the joint.
Figure 6B:
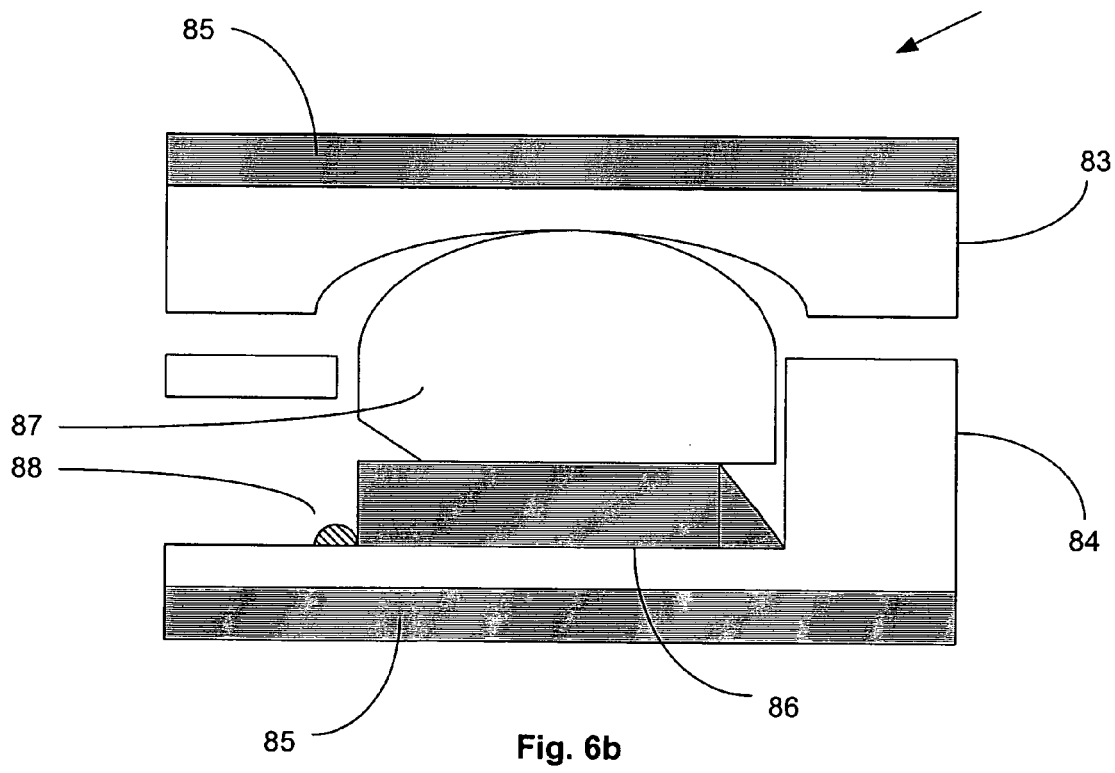
FIG. 6b is a side cross-sectional view of a banana-shaped, expandable intervertebral implant, illustrating the insertion of an expansion plate to expand the joint.

FIGS. 6a and 6b illustrate an alternative embodiment of a non-threaded expansion device. As shown in FIG. 6a, a banana-shaped artificial intervertebral implant 80 having a wide expansion slot 81 on either the medial or lateral side of the implant 80. Expansion plate 82 may be impacted into place through expansion slot 81 after artificial implant 80 has been properly placed within the intervertebral space. Similar to the previously described embodiments, the artificial implant comprises an upper body 83 and a lower body 84 in a substantially planar configuration, each having an osteoconductive scaffolding 85 machined on their superior and inferior surfaces, respectively. Note that the channel 86, as well as expansion plate 82, substantially conforms to the shape of the upper 83 and lower 84 bodies. Joint insert 87 may generally conform to the shape of the upper 83 and lower 84 bodies, however, the its preferred shape for the banana-shaped implant 80 is more oval, or even more preferably round, to provide improved biomechanical motion of the implant. The bottom floor of channel 86 may also employ a locking lip 88 to ensure that the expansion plate 82 is properly installed and to minimize the potential for dislocating expansion plate 82.

Figure 7A:
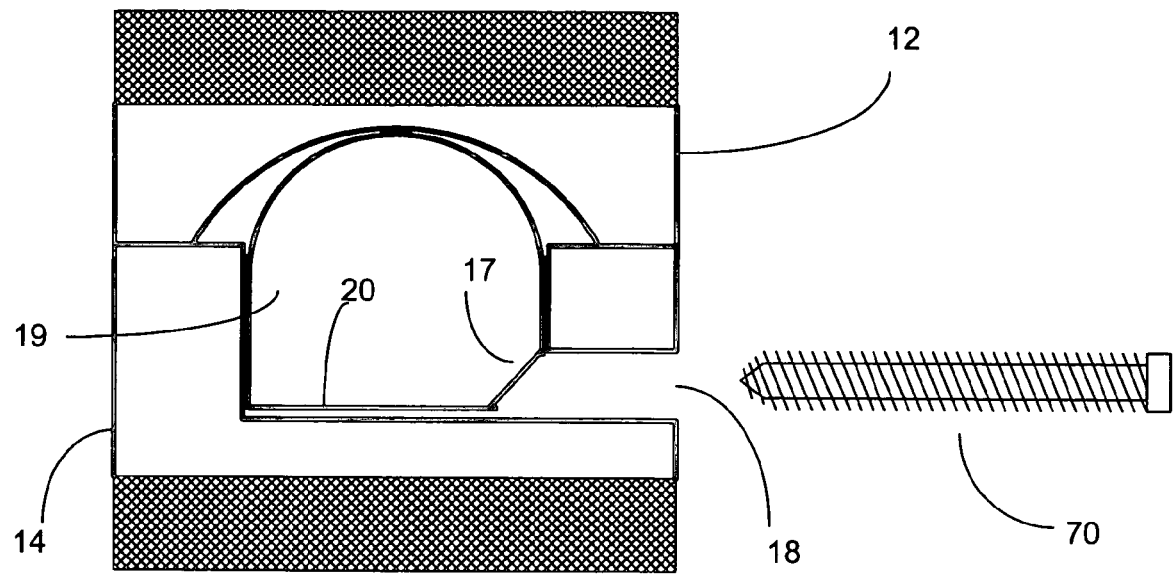
FIG. 7a is a cross-sectional view of an expandable intervertebral implant, prior to expansion.
Figure 7B:
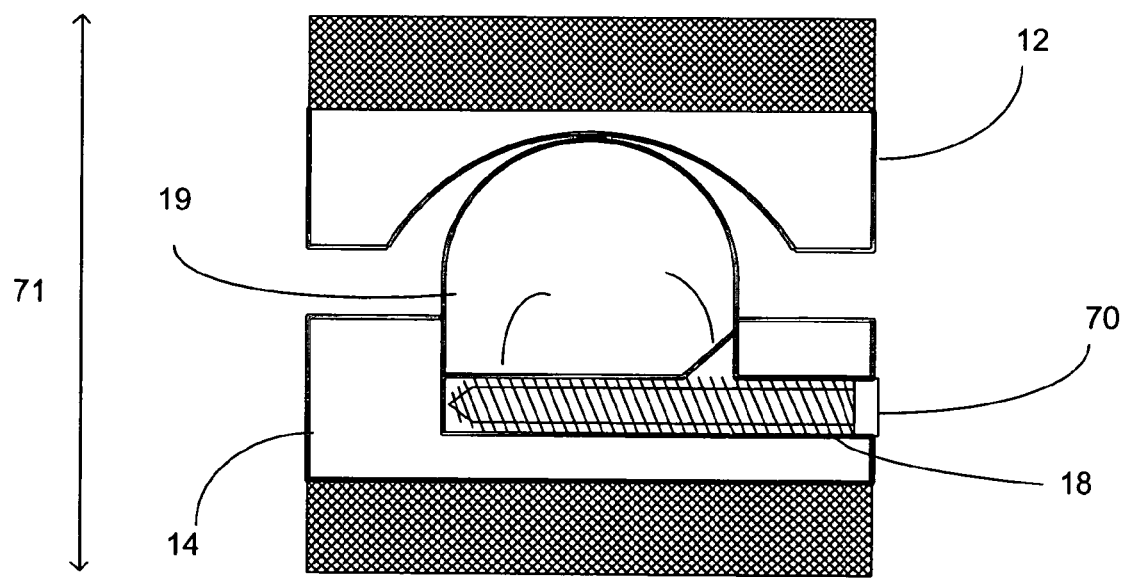
FIG. 7b is a cross-sectional view of an expandable intervertebral implant, following expansion.

FIGS. 7a and 7b illustrate the expansion of joint insert 19 in more detail. As shown in FIG. 7a and prior to expansion of joint insert 19, upper body 12 rests upon lower body 14 and the generally flat inferior surface 20 of joint insert 19 rests upon the bottom of channel 15, which extends along the lower body 14. Disposed along the generally flat inferior surface 20 of expandable joint insert 19 and adjacent to expansion slot 18, is a lifting notch 17 that engages with the expansion screw 70. Lifting notch 17 facilitates the lifting of expandable joint insert 19 and allows expansion screw 70 to come into contact with the generally flat inferior surface 20 of joint insert 19. Once inserted, as shown in FIG. 7b, the generally flat inferior surface 20 of expandable joint insert 19 rests upon expansion screw 70 and the upper body 12 is lifted above lower body 14 to the desired intervertebral disc height 71.

Figure 7C:
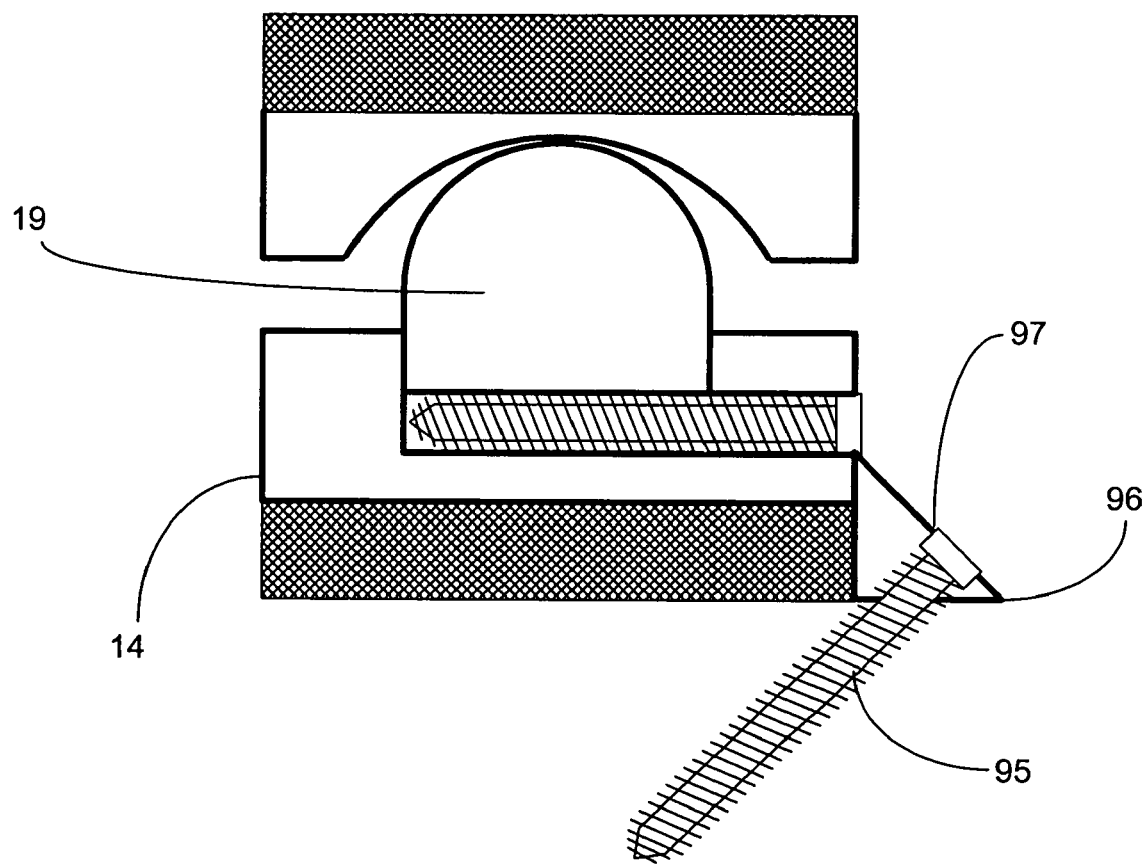
FIG. 7c is a cross-sectional view of an expandable intervertebral implant employing butress screws to secure the device.

After expansion of the joint insert 19, the implant may be secured in place by employing butress or similar types of screws. FIG. 7c illustrates one embodiment utilizing a butress screw 95. The lower body 14 has a lip 96 projecting from its inferior surface with one or more holes 97 defined therethrough. One or more screws 95 may be inserted through the lip 96 and secured into the vertebral body.

Figure 7D:
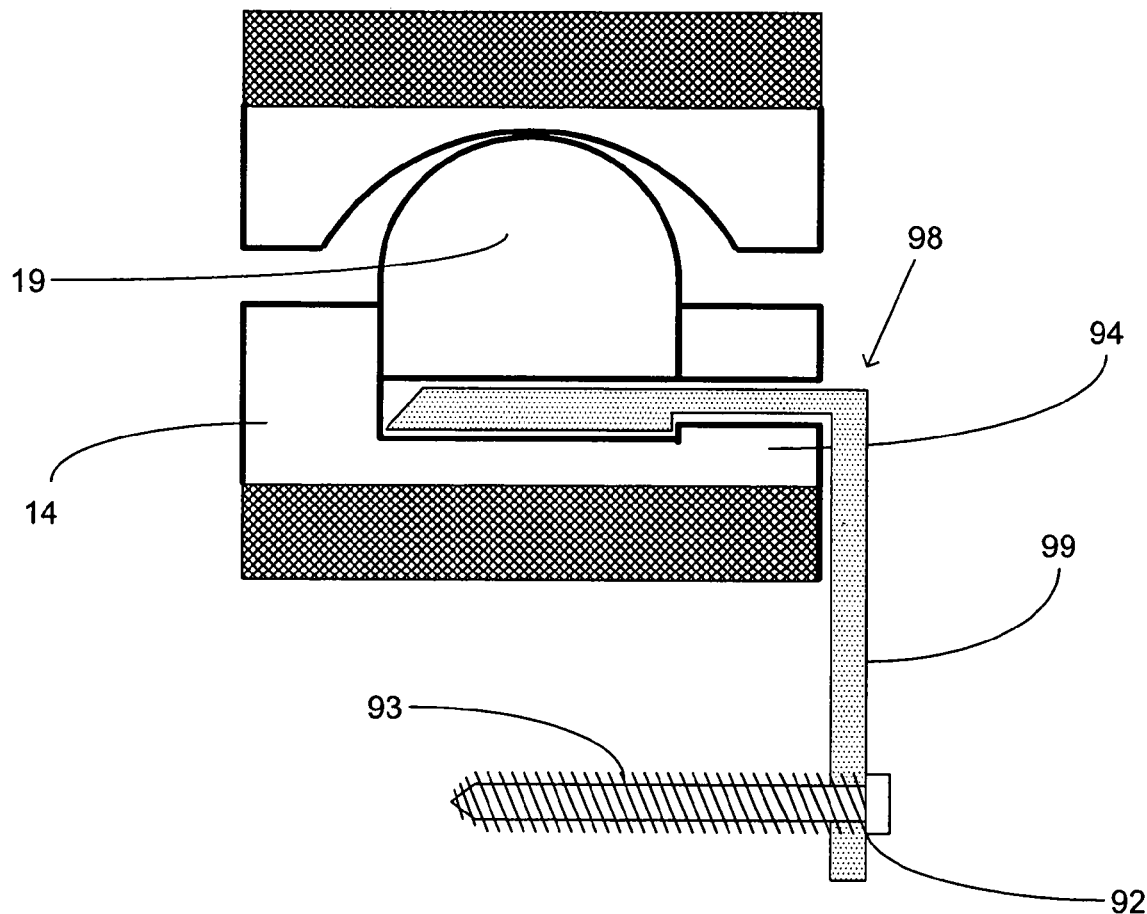
FIG. 7d is a cross-sectional view of an expandable intervertebral implant employing an expansion plate with a securing keel to secure the device.

Alternatively, when an expansion plate 98 is employed, as shown in FIG. 7d, the expansion plate 98 may comprise a downwardly projecting keel 99 with one or more holes 92 defined therethrough. After the expansion plate 98 is impacted into place, one or more screws 93 may be inserted through the keel 99 and secured into the vertebral body. The expansion plate 98 and lower body 14 may also comprise an interconnecting ridge 94 to secure the expansion plate 98 with lower body 14. Butress screws or the secured keel may be employed with any of the disclosed devices.

Figure 7E:
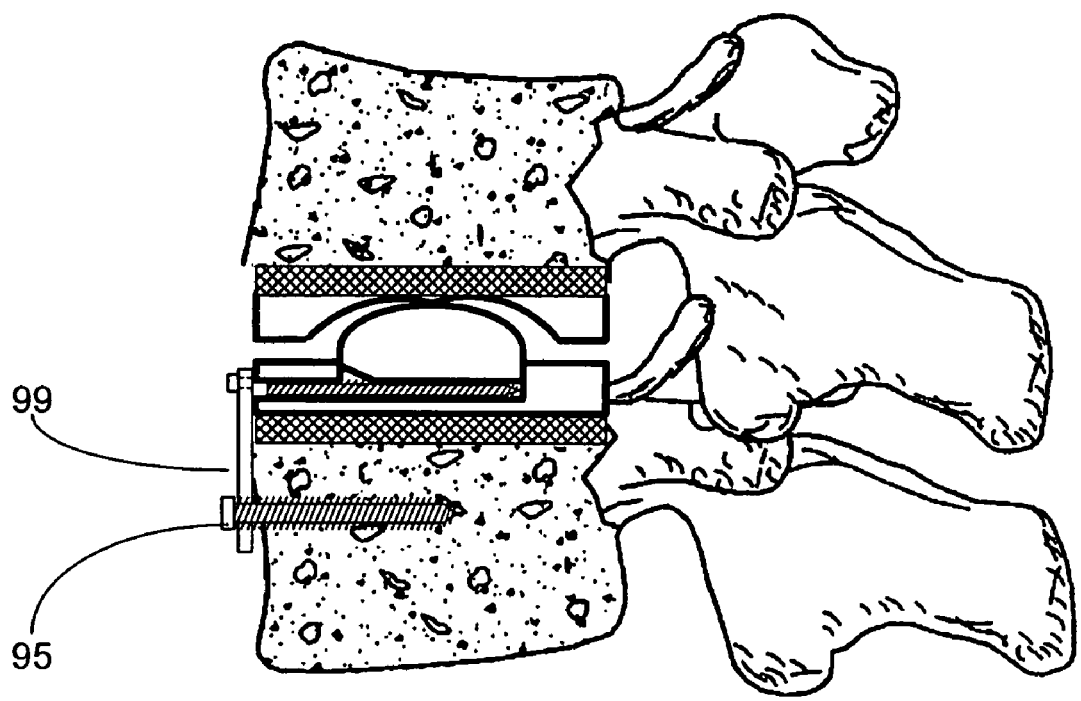
FIG. 7e is a side perspective of an expandable intervertebral implant employing a securing keel.

FIG. 7e illustrates a similar keel arrangement as described above that may be employed with any type of expansion device. One end of the keel 99 is secured onto the lower body 14 of any of the devices disclosed herein. The keel 99 can be rotated after placement of the device in the intervertebral space. After the keel 99 is rotated, it is secured to the vertebral body above or below by one or more screws 95.

Figure 8:
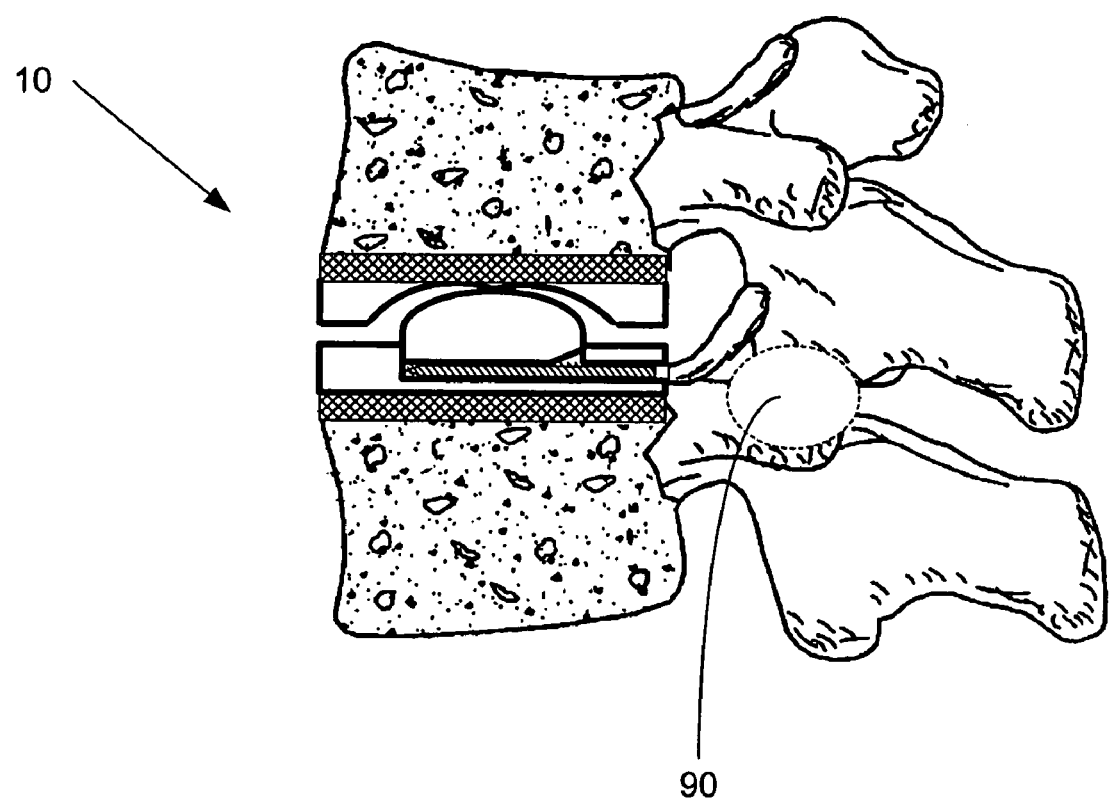
FIG. 8 is a side perspective view illustrating placement of an expandable intervertebral implant within an intervertebral space.

FIG. 8 shows an expandable artificial intervertebral implant 10 inserted into the spinal column. Note that the expandable artificial implant 10 is posteriorly inserted and expanded through void space 90, which is created by removal of a facet joint.

Figure 12A:
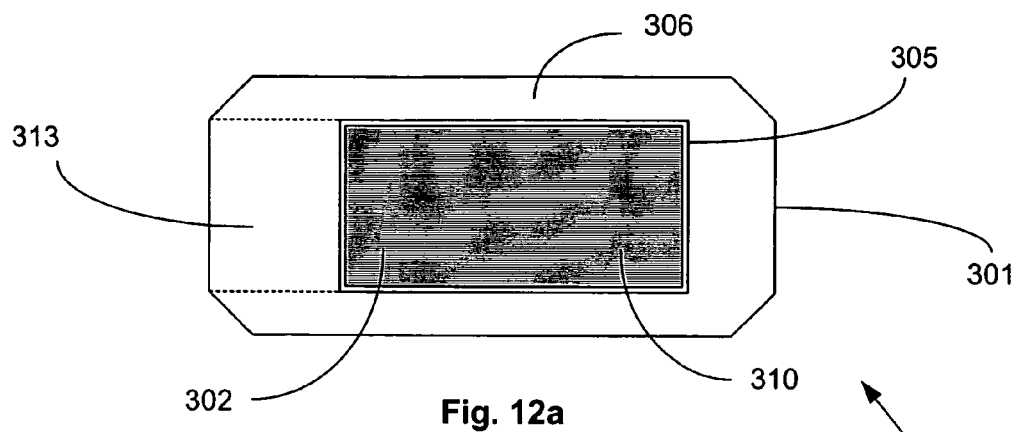
FIG. 12a is a top view of an expandable PLIF cage in accordance with the present invention.
Figure 12B:
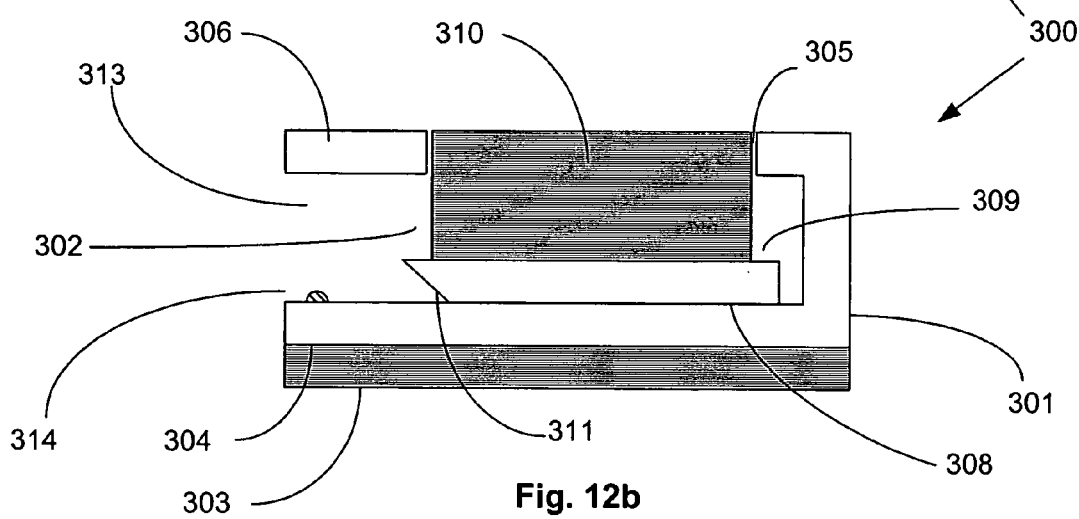
FIG. 12b is a side cross-sectional view of an expandable PLIF cage in accordance with the present invention prior to expansion.
Figure 12C:
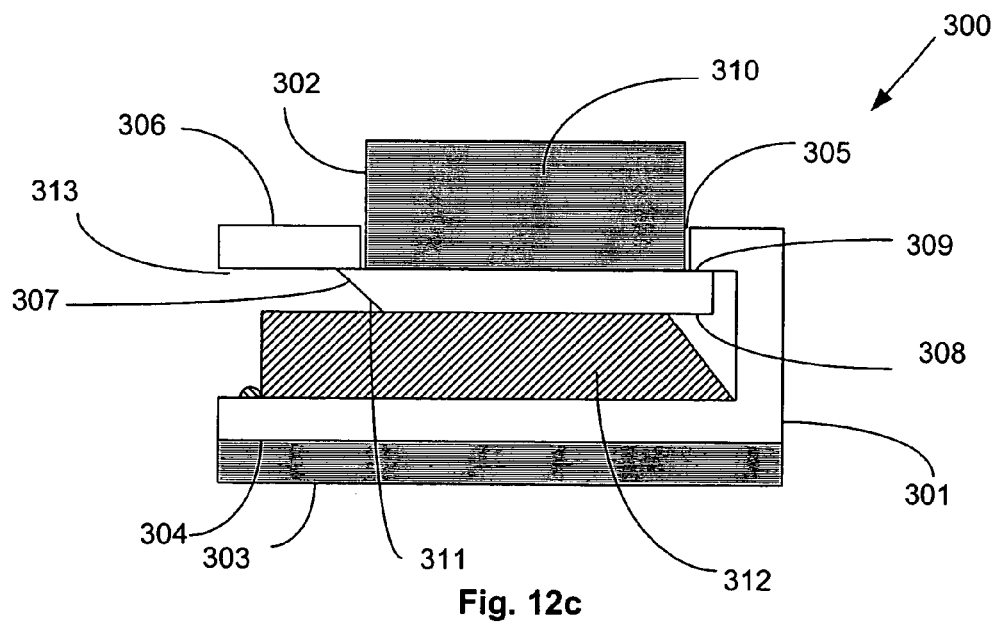
FIG. 12c is a side cross-sectional view of an expandable PLIF cage in accordance with the present invention following expansion.

The disclosed techniques of expanding an artificial implant by inserting an expansion plate or similar device may also be employed to expand a PLIF or TLIF cage. As shown in FIGS. 12a, 12b and 12c, a PLIF cage 300 is disclosed comprising a substantially rectangular external cage element 301 housing an internal expandable element 302. The PLIF cage element 301 has an osteoconductive mesh structure 303, in which an osteoconductive substance can be placed, on its inferior surface 304 and an expansion window 305 located on its superior surface 306. The internal expandable element 302 comprises a generally planar plate member 307 having an inferior 308 and superior surface 309. A second osteoconductive mesh structure 310 is secured upon the superior surface 309 of the planar plate member 307 of the internal expandable element 302. The inferior surface 308 of the planar plate member 307 has a lifting notch 311 to facilitate the expansion of the device upon installation of the expansion plate 312. The expansion plate 312 is inserted into the posteriorly located expansion slot 313 of the PLIF external cage element 301 and engages the lifting notch 311 of the planar plate member 307 of the internal expandable element 302. Locking lip 314 located within expansion slot 313 minimizes the potential of expansion plate 312 dislocation.

Figure 12D:
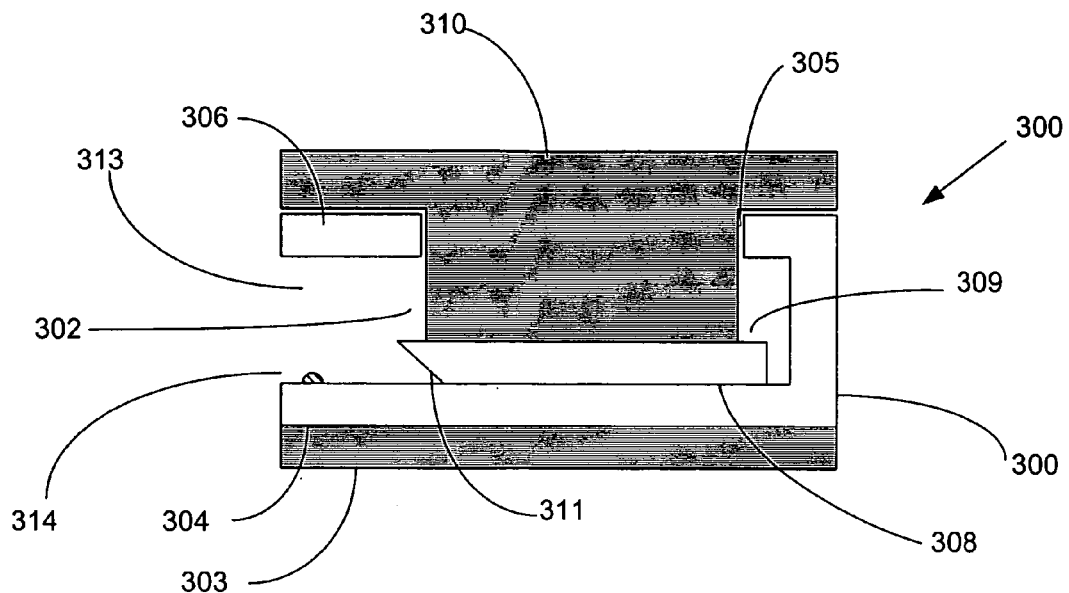
FIG. 12d is a side cross-sectional view of an expandable TLIF cage in accordance with the present invention prior to expansion.
Figure 12E:
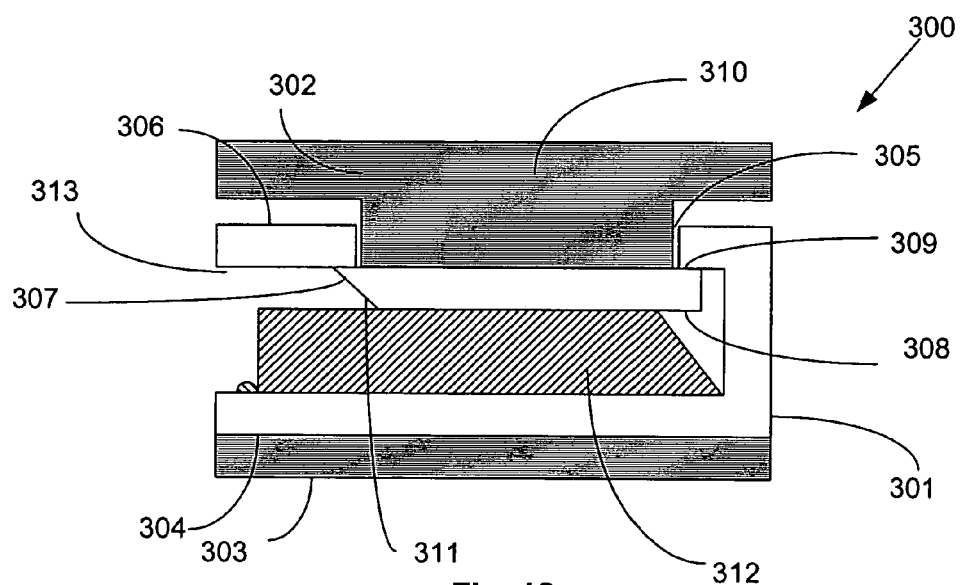
FIG. 12e is a side cross-sectional view of an expandable TLIF cage in accordance with the present invention following expansion.

FIGS. 12d and 12e show a TLIF cage similar to the PLIF cage described above. The primary difference between the TLIF cage and the PLIF cage is that the TLIF cage comprises a t-shaped cross-sectional osteoconductive mesh structure 310 secured upon the superior surface 309 of the planar plate member 307 of the internal expandable element 302 such that the osteoconductive mesh structure 310 overhangs the superior surface 306 of the external cage element 301. Thus providing more surface area between the osteoconductive mesh structure 310 and the bony endplates within the intervertebral space.

Figures 12F, 12G, 12H:
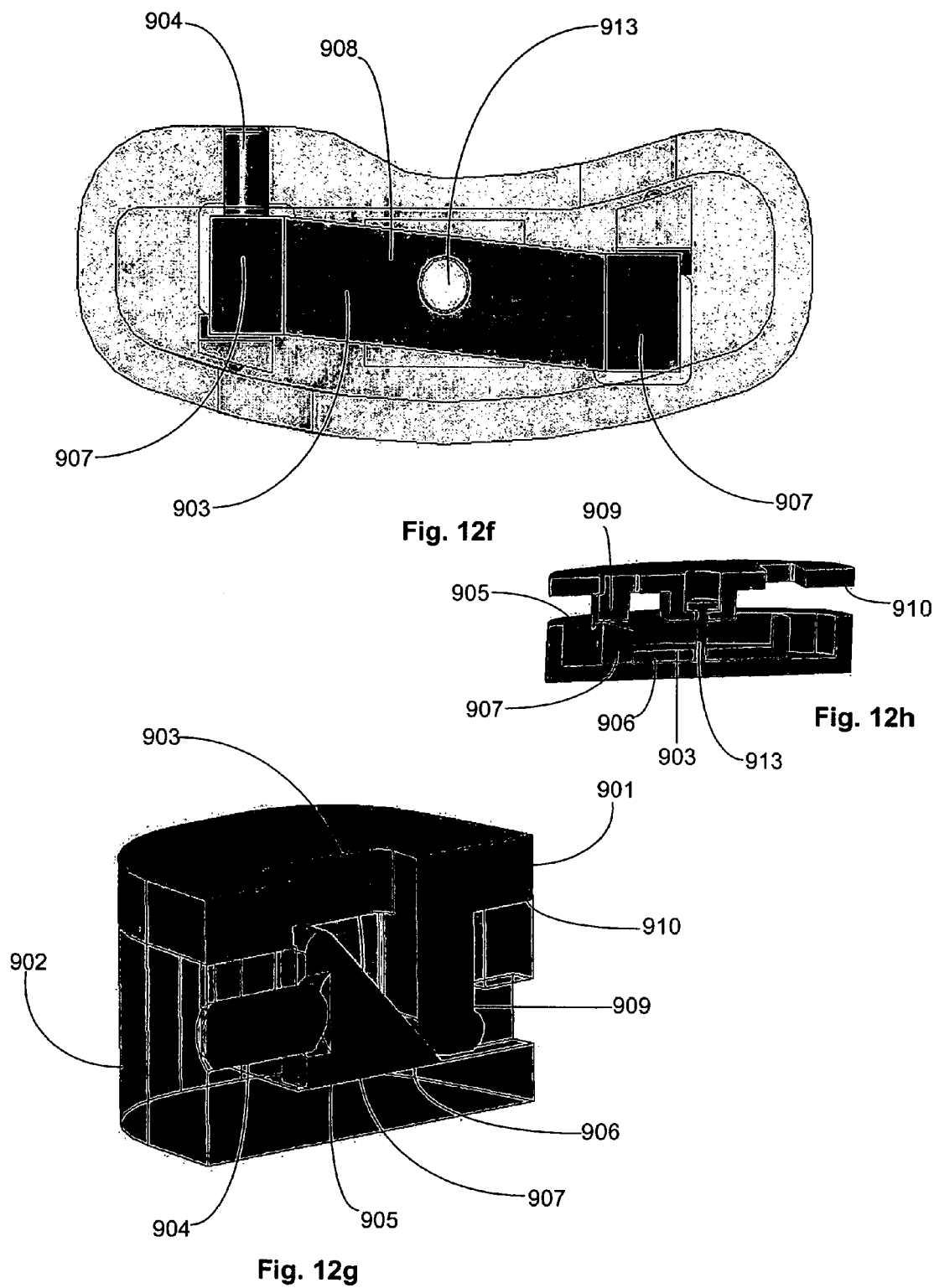
FIG. 12f is a top view of another expandable cage in accordance with the present invention.
FIG. 12g is a side cross-sectional view of the expandable cage of FIG. 12f.
FIG. 12h is a cross-sectional view of the expandable cage of FIG. 12f featuring a captive peg.
Figure 12I:
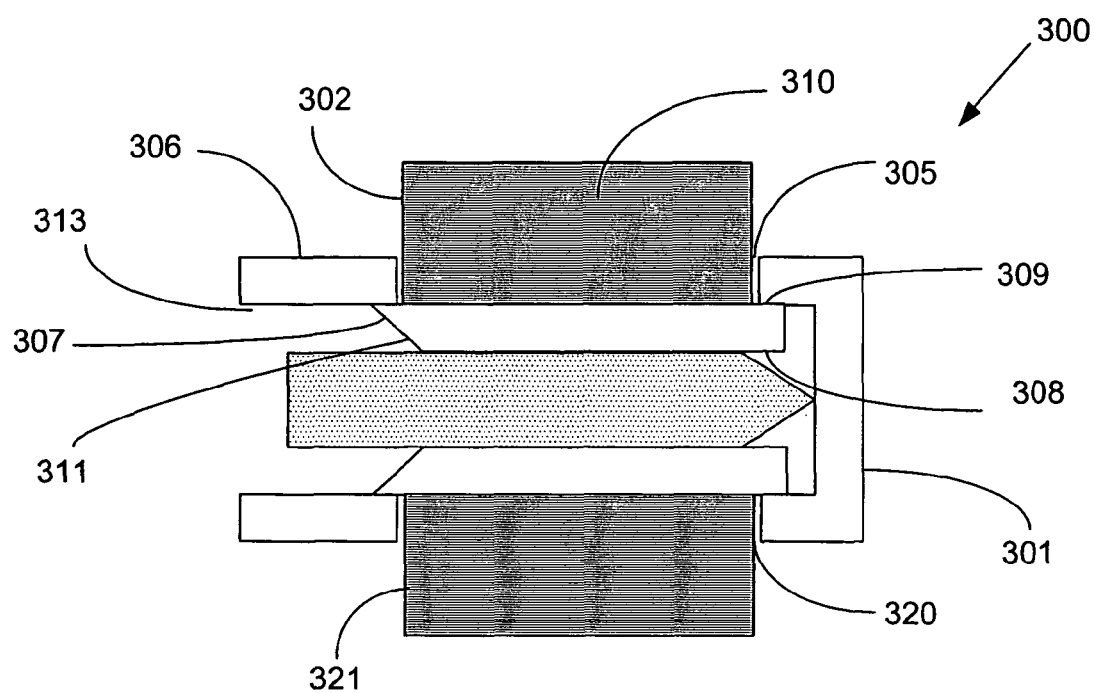
FIG. 12i is a cross-sectional view of an expandable cage featuring a two-dimensional expansion joint.

Expandable cages may also be expanded in two dimensions as illustrated in FIG. 12i. Cage element 301 may further comprise an expansion window 320 through its inferior surface and a second internal expandable element 321. As expansion plate 312 is impacted into the device, both internal expandable elements 302, 321 are pushed through their respective expansion windows 305, 320.

FIGS. 12f and 12g illustrate another preferred embodiment of an expandable cage 900 utilizing the expansion principles disclosed herein. The embodiment generally comprises four parts: an upper body 901, a lower body 902, an expansion joint insert 903, and an expansion screw 904 or similar device. The placement of the device in the spine will determined the preferred shape of the upper and lower bodies 901, 902. The lower body 902 has a recessed channel 905 on it superior surface 906 that houses the joint insert 903 similar to the previously described functional implants. However, the joint insert 903 for this embodiment does not lift above the recessed channel 905 in the lower body 902.

The joint insert 903 preferably has a substantially flat inferior surface 906 and one or more angled projections 907 extending upward from its superior surface 908. These angled projections articulate with similar angled projections 909 extending downward from the inferior surface 910 of the upper body 901. As the expansion screw 911 is inserted into the expansion hole 912 in the lower body 902, it forces the joint insert 903 to rotate within the recessed channel 905. As the joint insert 903 rotates, the upper body 901 lifts above the lower body 902 as the angled projections 909 of the upper body 901 slide up the angled projections 907 of the joint insert 903. A captive peg 913 maybe employed to limit the maximum expansion height and to control rotation of the joint insert 903 within the recessed channel 905.

Figure 9A:
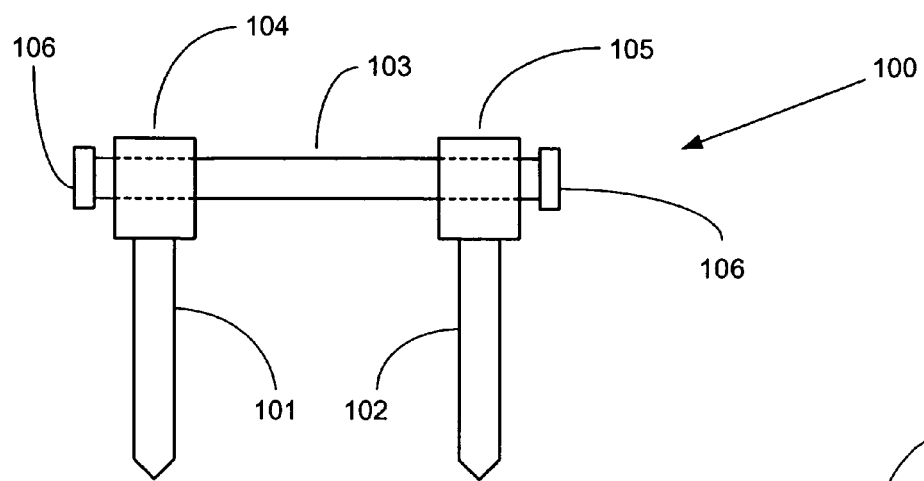
FIG. 9a is a side view of an artificial facet joint of the present invention, featuring a rod with two washer-type heads.

One preferred embodiment of an artificial facet joint 100 in accordance with the present invention is shown in FIG. 9a. Artificial facet joint 100 comprises an upper pedicle screw 101 and a lower pedicle screw 102. Rod 103 is retained within the head 104 of upper pedicle screw 101 and the head 105 of lower pedicle screw 102. Rod 103 has washer-type ends 106 that allows for posterior compression, but not extension.

Figure 9B:
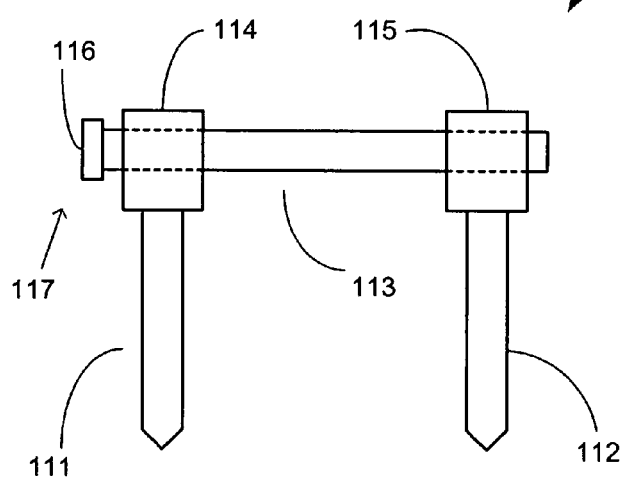
FIG. 9b is a side view of an artificial facet joint of the present invention, featuring a rod with a single washer-type head.
Figure 9C:
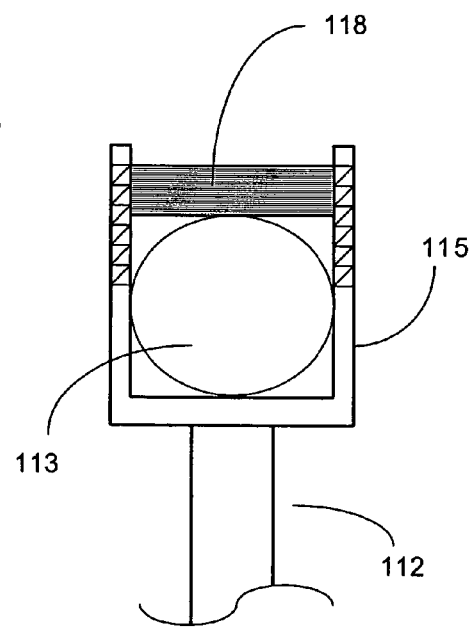
FIG. 9c is a cross-sectional view of a pedicle screw featuring a locking screw head.

Another preferred embodiment of an artificial facet joint 110 is shown in FIG. 9b. Rod 113 comprises a single washer-type end 116 on its lower end 117. The head 115 of upper pedicle screw 112 has a threaded locking screw 118, as shown in FIG. 9c, that holds rod 113 in place and prohibits the head 115 of pedicle screw 112 from swiveling, but allows rod 113 to rotate and translate through the head 115 of pedicle screw 102.

Figure 9D:
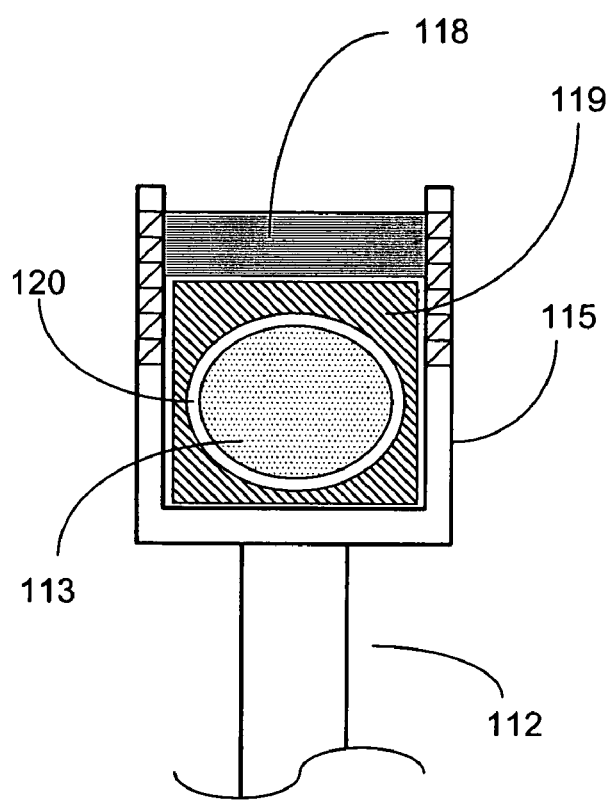
FIG. 9d is a cross-sectional view of a pedicle screw featuring a head-locking insert.

FIG. 9d illustrates a head-locking insert that can be used in conjunction with a pedicle screw having a locking type head. The head-locking insert 119 has a similar shape to the head 115 of the pedicle screw. The insert 119 is preferably of solid construction having a hole 120 defined through the insert 119 that substantially aligns with the hole defined through the head 115 of the pedicle screw. As the set screw 118 is engaged into the head 115 of the set screw, force is applied onto the top of the insert 119 and transferred to the bottom of the head 115. The force locks the head 115 of the pedicle screw, as with conventional locking pedicle screws; however, the force is not transferred to rod 113. With no force transferred to the rod 113, it is allowed to freely rotate and translate through the head 115 of the pedicle screw. Alternatively, a shorter insert 119 may be employed that does not prohibit the multi-axial motion of the pedicle screw head. The shorter insert 119 will not transfer the force to the bottom of the head, will retain the rod within the head.

Figure 10A:
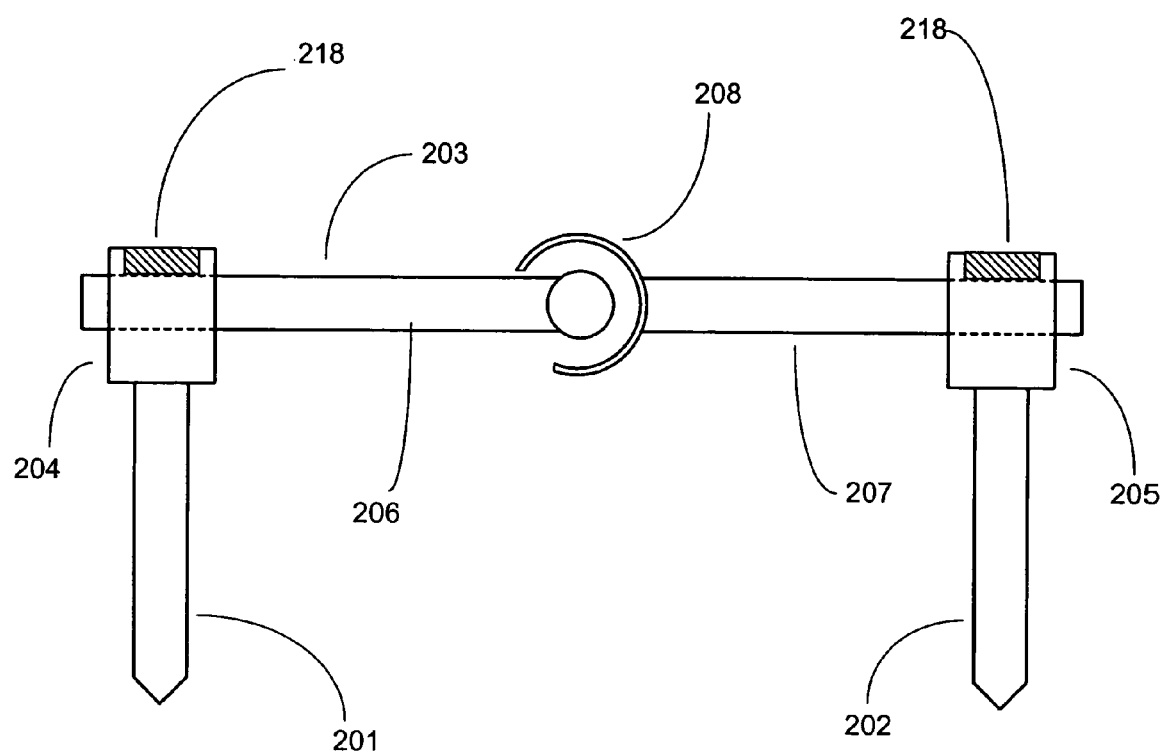
FIG. 10a is a side view of an artificial facet joint of the present invention, featuring a rod having a ball joint.

Another preferred embodiment of an artificial facet joint 200 is shown in FIG. 10a. Artificial facet joint 200 generally comprises an upper pedicle screw 201 and a lower pedicle screw 202 and rod 203 retained within the heads of pedicle screws 201, 202. Both pedicle screws 201, 202 are secured with locking screws 218 that prevent the heads 204, 205 of pedicle screws 201, 202 from swiveling, but allow rotation and translation of rod 203. Rod 203 comprises two rod members 206, 207 connected via a ball joint 208. Ball joint 208 allows for a generally upward rotation, away from the bony surfaces of the vertebrae to which they are secured, but prohibit a generally downward rotation, which would bring the ball joint in contact with the vertebrae to which they are secured.

Figure 10B:
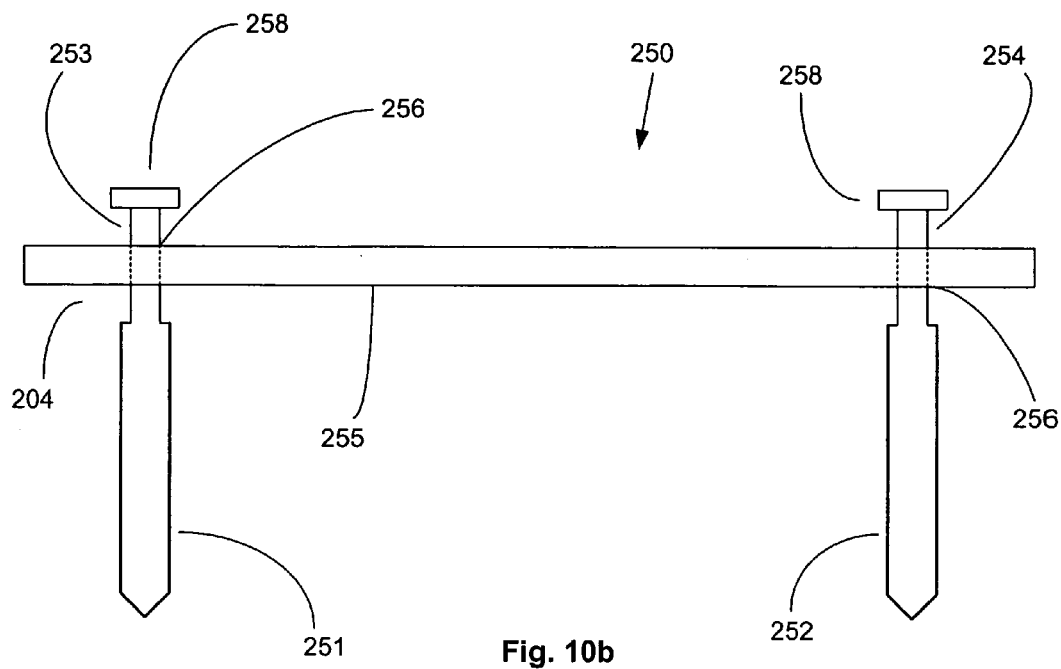
FIG. 10b is a side view of an artificial facet joint featuring a retaining plate.
Figure 10C:
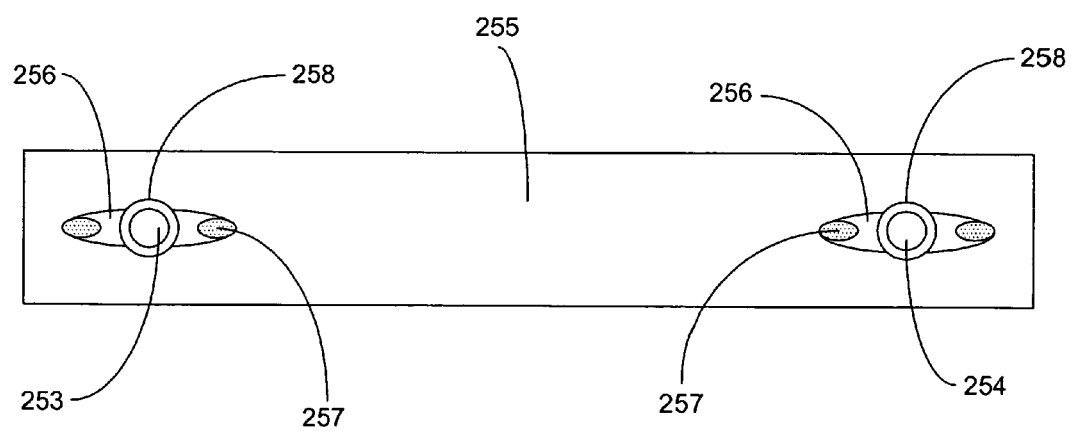
FIG. 10c is a top view of an artificial facet joint featuring a retaining plate.

Another preferred embodiment of an artificial facet joint is shown in FIGS. 10b and 10c. In this preferred embodiment, the artificial facet joint 250 generally comprises an upper 251 and lower pedicle screw 252 having post-type heads 253, 254. Rather than the previously described rod, a retaining plate 255 is employed. Elongated holes 256 are defined through the retaining plate 255, which are positioned upon the post-type heads 253, 254 of the pedicle screws 251, 252. The post-type heads 251, 252 are allowed to move within the elongated holes 256, providing limited range of motion. Employing cushioning pads 257 made of rubber or similar biocompatible material may dampen the movement of the plate. The post-type heads 251, 252 may also comprise threaded or lockable caps 258 to prevent dislocation of the plate 255 from the post-type heads 251, 252.

FIG. 10d illustrates a pedicle screw having a post-type head 253 used in conjunction with a pedicle screw having a locking or non-locking type head 260. Retaining plate 255 is formed with a rod 261 on one end, which is slidingly positioned through pedicle screw 260.

As shown in FIG. 10e and 10f, the post-type heads 272 of the pedicle screws used in conjunction with the retaining plate 255 may also exhibit multi-axial motion. The post-type head 272 is attached to the pedicle screw 270 with a ball joint 271.

FIG. 10f shows a spacer 274 disposed below retaining plate 255 that allows for rotation of ball joint 271.

Figure 11:
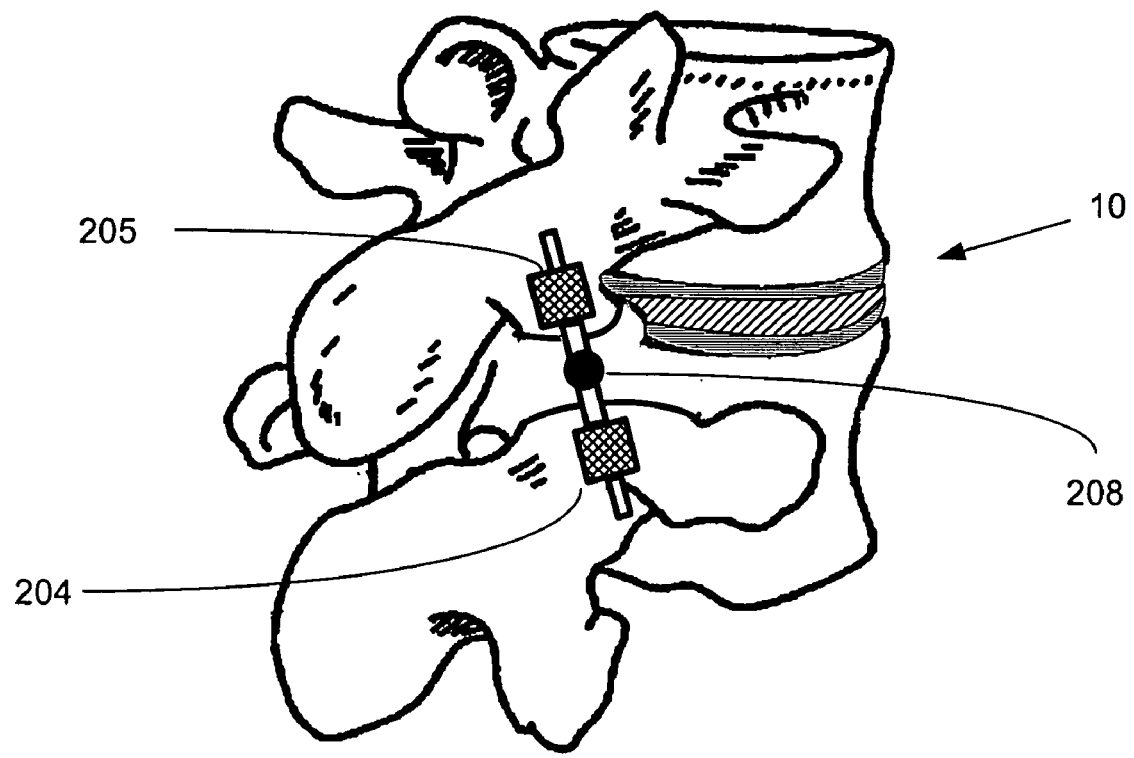
FIG. 11 is a posterior view of the spine after reconstruction and implantation of an artificial functional spinal unit including an expandable intervertebral implant and an artificial facet joint.

FIG. 11 shows the artificial facet joint 200 of FIG. 10 in place on the spinal column. Note that artificial intervertebral implant 10 has been posteriorly placed within the intervertebral space through the void created by the surgical removal of the natural facet joint. In addition, ball joint 208 generally rotates in the posterior (upward) direction during posterior compression to prevent impact upon the bony surfaces of the spine.

Figure 13A:
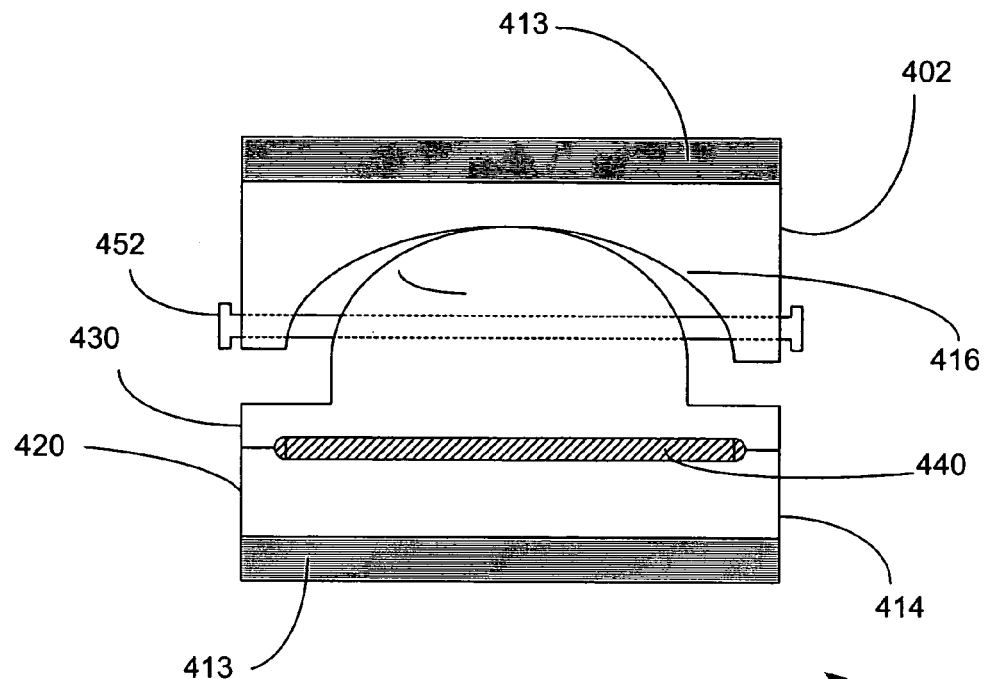
FIG. 13a is a posterior view of a banana-shaped lordotic expandable intervertebral implant.

FIGS. 13a, 13b, 14a and 14b illustrate a lordotic, banana-shaped expandable artificial intervertebral implant 400. The lumbar spine is lordotic, thus the anterior disc height is naturally larger than the posterior disc height. Therefore, an expandable artificial intervertebral implant for the lumbar spine must be capable of expanding into a lordotic position. FIG. 13a shows the lordotic expandable artificial intervertebral implant 400 from a posterior view. Lordotic expandable artificial intervertebral implant 400 generally comprises an upper body 412 and a lower hinged body 414 in a substantially planar configuration prior to expansion. The superior surface 402 of the upper body 412 and the inferior surface 404 of the lower hinged body 414 comprise an osteoconductive scaffolding 413 through which the bone may ultimately grow. The upper body 412 has a substantially concave inferior surface 416.

The lower hinged body 414 comprises a lower portion 420 and an upper portion 430. Lower portion 420 and upper portion 430 are posteriorly hinged via hinge 440. Hinge 440 effectively fixes the posterior disk height 460 (shown in FIG. 14b). Upper portion 430 of hinged body 414 has a generally flat inferior surface 431 and a substantially convex superior surface 432. The lower portion 420 has a substantially planar configuration prior to expansion. Located at the anterior end 421 of lower portion 420 is a rotational lifting mechanism 422. Once placed in the intervertebral space, the rotational lifting leg is rotationally engaged, thus lifting the anterior end 421 of the expandable artificial intervertebral implant 400 to achieve the desired anterior disc height 470 and proper lordosis. Securing notch 425 is located on the anterior end 421 of the upper portion 430 of hinged body 414. Securing notch 425 engages with rotational lifting mechanism 422 once the expandable artificial intervertebral implant 400 has been expanded. The height of rotational lifting mechanism 422 is determined by the desired proper lordosis when the intervertebral implant 400 is under neutral load.

Figure 14A:
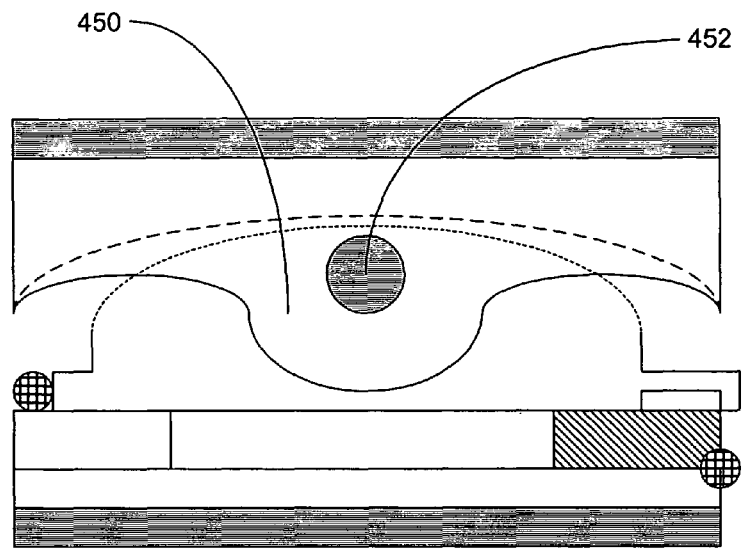
FIG. 14a is a lateral view of a banana-shaped lordotic expandable intervertebral implant prior to expansion.
Figure 14B:
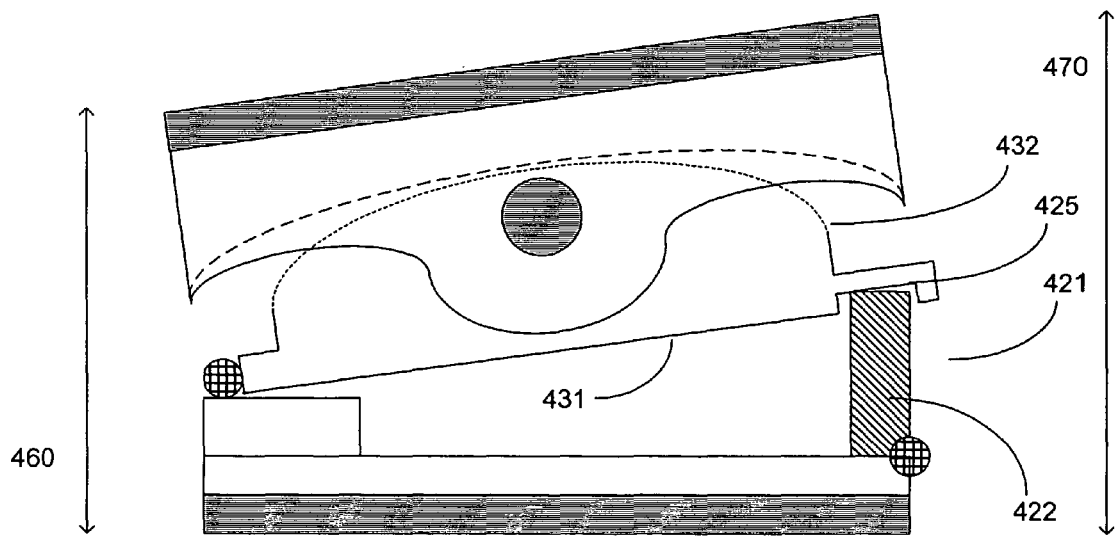
FIG. 14b is a lateral view of a banana-shaped lordotic expandable intervertebral implant following expansion.

Upper body 412 has a substantially concave inferior surface 416 that articulates with the substantially convex superior surface 432 of upper portion 430 of lower hinged body 414. When viewed in the medial or lateral direction, as shown in FIGS. 14a and 14b, upper body 412 has a downwardly projecting lobe 450 for the attachment of safety bar 452. Safety bar 452 secures upper body 412 to upper portion 430 of lower hinged body 414 and minimizes the possibility of dislocation.

Figure 13B:
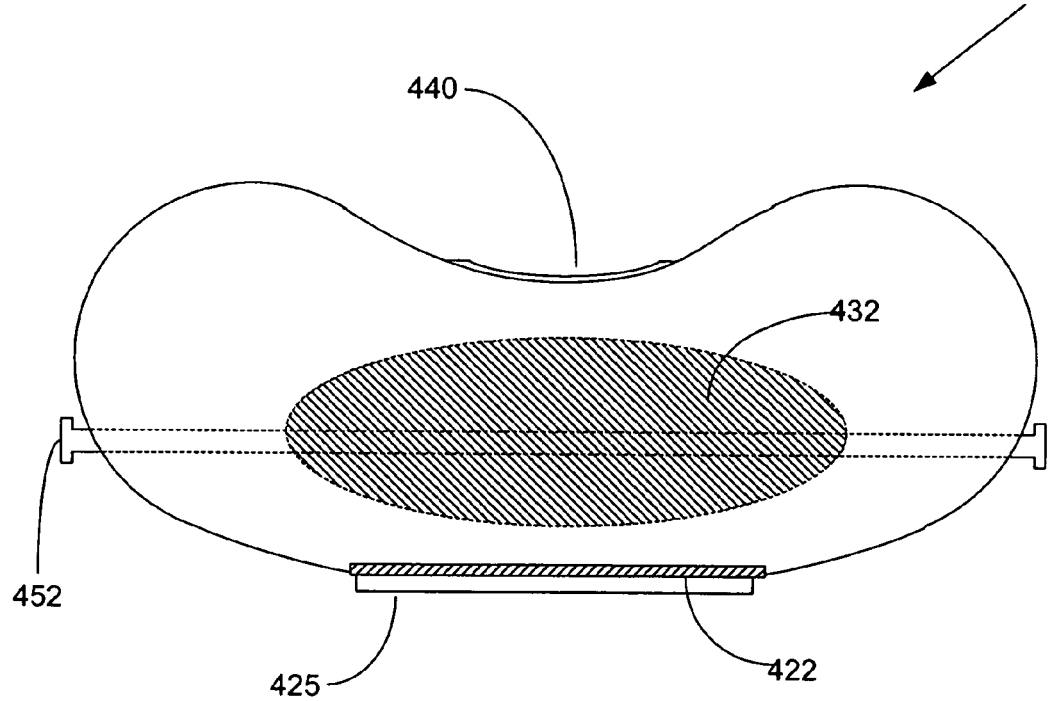
FIG. 13b is a top view of a banana-shaped lordotic expandable intervertebral implant.

FIG. 13b is a top view of lordotic expandable artificial intervertebral implant 400 illustrating the placement of posterior hinge 440, rotational lifting mechanism 422, and safety bar 452 affixed through upper body 412 and upper portion 430 of lower hinged body 414.

Figure 15A:
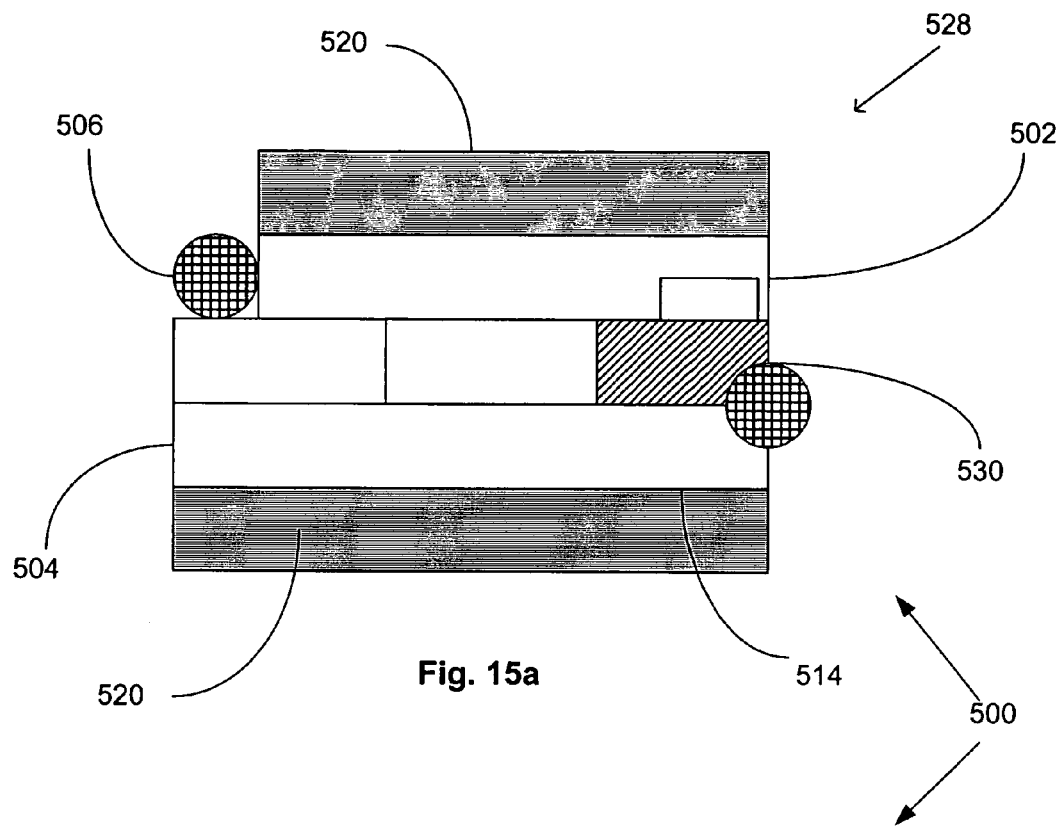
FIG. 15a is a side cross-sectional view of an expandable lordotic cage prior to expansion.
Figure 15B:
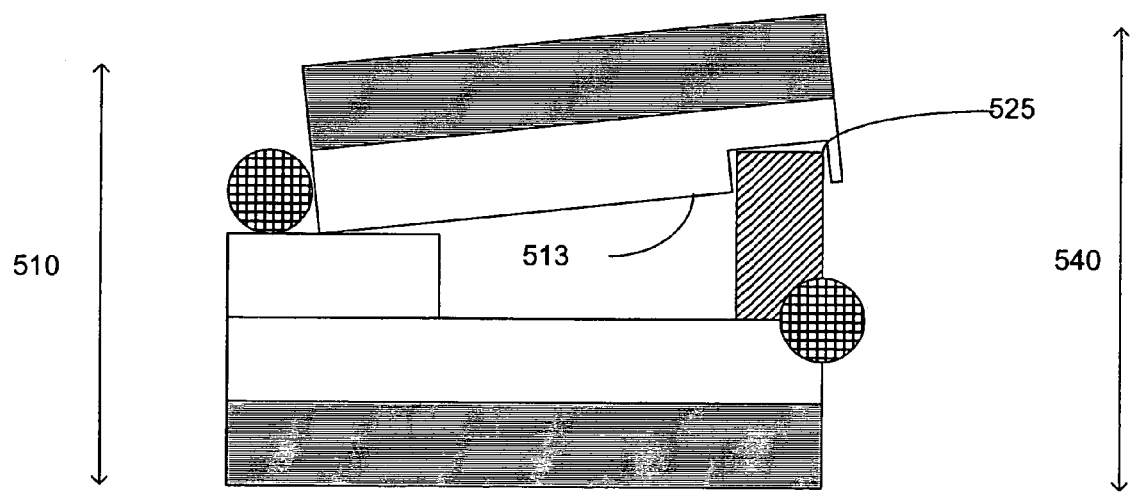
FIG. 15b is a side cross-sectional view of an expandable lordotic cage following expansion.

The rotational lifting mechanism described above may also be employed to achieve proper lordosis with an expandable PLIF and TLIF cage, as shown in FIGS. 15a and 15b. Cage 500 is shown prior to expansion in FIG. 15a and expanded in FIG. 15b. Cage 500 comprises an upper body 502 and a lower body 504. Hinge 506 posteriorly connects upper body 502 to lower body 504 and effectively fixes posterior disc height 510 upon expansion of cage 500. The superior surface 512 of upper body 502 and the inferior surface 514 of lower body 504 may include an osteoconductive scaffolding or mesh 520 as previously described. Expansion of cage 500 is accomplished via rotational lifting mechanism 530, which engages with securing notch 525, located on the anterior end 528 of the inferior surface 513 of upper body 502, and minimizes the potential for dislocation. The height of rotational lifting mechanism 530, which effectively fixes anterior disc height 540, is determined by the desired proper lordosis.

Figure 16A:
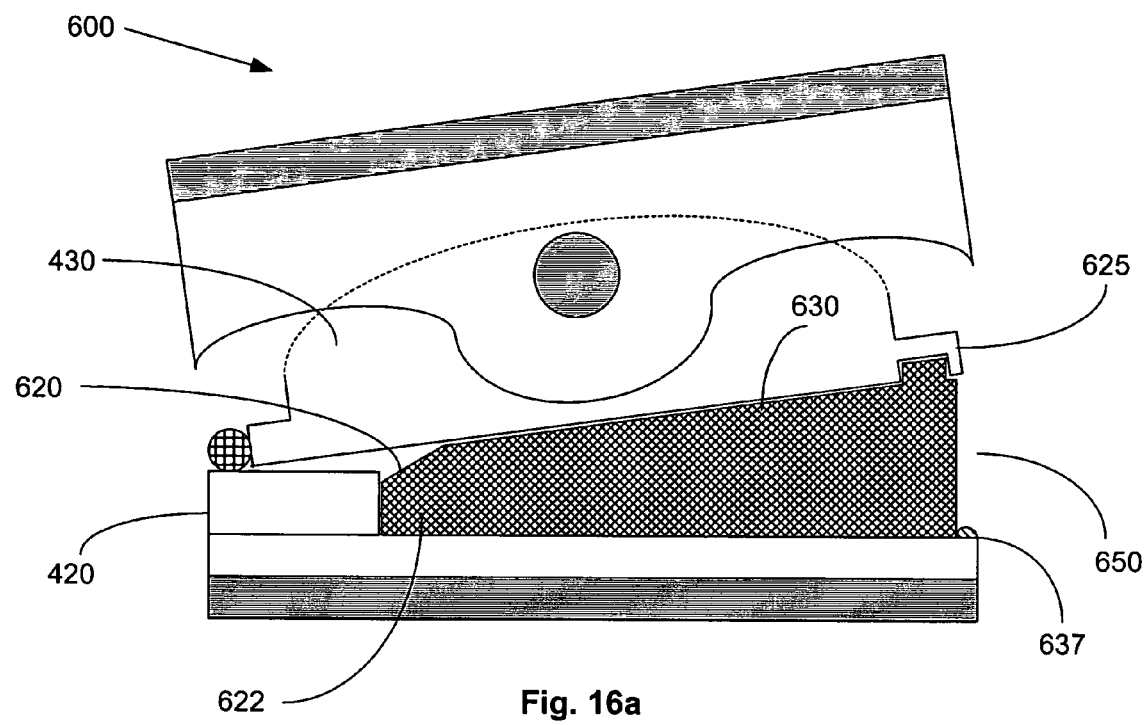
FIG. 16a is a lateral view of a banana-shaped lordotic expandable intervertebral implant featuring an inclined expansion plate.
Figure 16B:
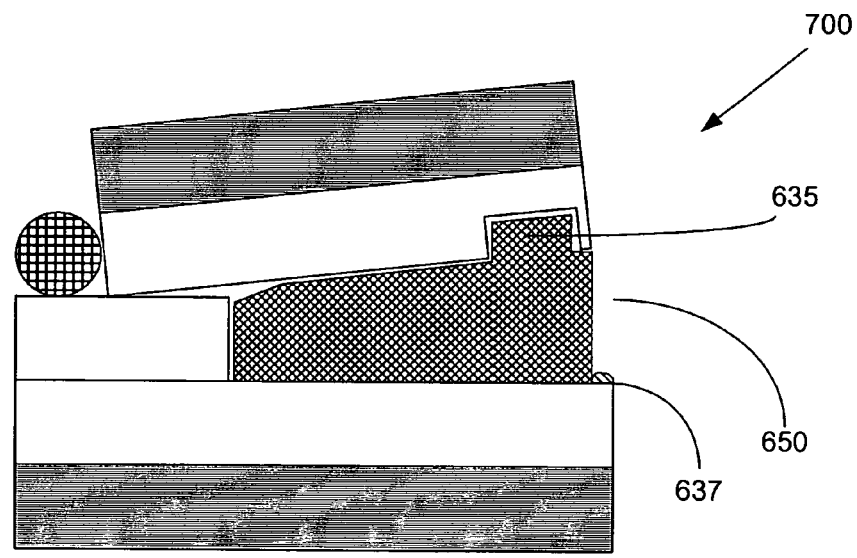
FIG. 16b is a side cross-sectional view of an expandable lordotic cage featuring an inclined expansion plate.

Another preferred embodiment of an expandable lordotic artificial intervertebral implant is illustrated in FIGS. 16a and 16b. Lordotic expandable intervertebral implant 600 and lordotic cage 700 both utilize an inclined expansion plate 650 to achieve proper lordosis. Both devices are similar to those described above with the exception of the expansion device and reference is made to FIGS. 14a and 14b for lordotic expandable intervertebral implant 600 and FIGS. 15a and 15b for lordotic cage 700 for elements of the intervertebral implants already identified. Expansion plate 650 is generally wedged-shaped and comprises a lifting notch 620 on its posterior end 622 to facilitate expansion. As shown in FIG. 16a, expansion plate 650 is installed between the upper portion 430 and lower portion 420 of lower hinged body 414. Located on the superior surface 630 at the anterior end 624 is securing ridge 635. Securing ridge 635 engages with securing notch 625 similar to the rotational lifting mechanism described above. Located on the anterior superior surface of lower portion 420 of lower hinged body 414 is a locking lip 637, which minimizes the potential of dislocating inclined expansion plate 650. FIG. 16b illustrate the use of expansion plate 650 in conjunction with lordotic cage 700.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An intervertebral implant for a human spine, comprising:
   a cage element comprising a superior surface and an inferior surface, wherein the inferior surface of the cage element is configured to support a first vertebra of the human spine to inhibit movement of the first vertebra towards a second vertebra, and wherein the superior surface of the cage element comprises a first opening;
   an insert comprising a support surface for the second vertebra, wherein the support surface, during use, supports at least a portion of the second vertebra above and away from the superior surface of the cage element and inhibits movement of the second vertebra towards the first vertebra, and wherein the insert, during use, is inserted at least partially into the cage element; and
   an expansion member that, during use, is inserted in the cage element through an opening in a side of the cage element to expand the intervertebral implant by elevating the insert to move a portion of the insert through the first opening in the superior surface of the cage element so that at least a portion of the support surface of the insert is raised above and away from the superior surface of the cage to support at least a portion of the second vertebra above and away from the superior surface of the cage element.

2. The intervertebral implant of claim 1, wherein the intervertebral implant is configured such that the direction of movement of the expansion member is substantially perpendicular to the direction of movement of the insert.

3. The intervertebral implant of claim 1, wherein the expansion member is configured to be advanced between an interior surface of the cage element and the inferior surface of the insert.

4. The intervertebral implant of claim 1, wherein the support surface of the insert comprises osteoconductive mesh structure.

5. The intervertebral implant of claim 1, wherein an interior surface of the cage element comprises a raised portion configured to inhibit backout of the expansion member after expansion of the intervertebral implant.

6. The intervertebral implant of claim 1, wherein the expansion member comprises an angled portion configured to engage an angled portion of the insert to facilitate insertion of the expansion member in the cage element.

7. The intervertebral implant of claim 1, wherein the support surface of the insert comprises at least a majority of a surface of the intervertebral implant that is configured to support the second vertebra.

8. The intervertebral implant of claim 1, wherein the support surface comprises a substantially planar surface that supports at least a portion of the second vertebra above and away from the superior surface of the cage element and inhibits movement of the second vertebra towards the first vertebra during use.

9. The intervertebral implant of claim 1, wherein the support surface of the insert comprises a substantially planar surface of sufficient cross-sectional area to support the second vertebra above and away from the superior surface of the cage element during use.

10. The intervertebral implant of claim 1, wherein, during use, the support surface of the insert supports the second vertebra above and away from the superior surface of the cage element such that the second vertebra does not contact the superior surface of the cage element.

11. The intervertebral implant of claim 1, wherein the expansion member is at least partially removed from the cage element after being inserted in the cage element through an opening in a side of the cage element to expand the intervertebral implant.

12. An intervertebral implant for a human spine, comprising:
   a cage element comprising a superior surface and an inferior surface, wherein the inferior surface of the cage element is configured to support a first vertebra of the human spine to inhibit movement of the first vertebra towards a second vertebra, and wherein the superior surface of the cage element comprises an opening;
   an insert comprising an inferior surface and a support surface for the second vertebra, wherein the support surface, during use, supports the at least a portion of the second vertebra above and away from the superior surface of the cage element and inhibits movement of the second vertebra towards the first vertebra, wherein the insert, during use, is inserted at least partially into the cage element such that at least a portion of the inferior surface of the insert is below the superior surface of the cage element and at least a portion of the support surface of the insert is above the superior surface of the cage element to support at least a portion of the second vertebra above and away from the superior surface of the cage element; and
   an expansion member that, during use, is inserted in the cage element through an opening in a side of the cage element to elevate at least a portion of the insert through the opening in the superior surface of the cage element so that the support surface of the insert is raised above and away from the superior surface of the cage to support at least a portion of the second vertebra above and away from the superior surface of the cage element.

13. The intervertebral implant of claim 12, wherein the intervertebral implant is configured such that the direction of movement of the expansion member is substantially perpendicular to the direction of movement of the insert.

14. The intervertebral implant of claim 12, wherein the expansion member is configured to be advanced between an interior surface of the cage element and the inferior surface of the insert.

15. The intervertebral implant of claim 12, wherein the support surface of the insert comprises osteoconductive mesh structure.

16. The intervertebral implant of claim 12, wherein an interior surface of the cage element comprises a raised portion configured to inhibit backout of the expansion member after insertion of the expansion member.

17. The intervertebral implant of claim 12, wherein the expansion member comprises an angled portion configured to engage an angled portion of the insert to facilitate insertion of the expansion member in the cage element.

18. The intervertebral implant of claim 12, wherein the support surface of the insert comprises at least a majority of a surface of the intervertebral implant that is configured to support the second vertebra.

19. The intervertebral implant of claim 12, wherein the support surface comprises a substantially planar surface that supports at least a portion of the second vertebra above and away from the superior surface of the cage element and inhibits movement of the second vertebra towards the first vertebra during use.

20. The intervertebral implant of claim 12, wherein the support surface of the insert comprises a substantially planar surface of sufficient cross-sectional area to support the second vertebra above and away from the superior surface of the cage element during use.

21. The intervertebral implant of claim 12, wherein, during use, the support surface of the insert supports the second vertebra above and away from the superior surface of the cage element such that the second vertebra does not contact the superior surface of the cage element.

22. The intervertebral implant of claim 12, wherein the expansion member is at least partially removed from the cage element after being inserted in the cage element through the opening in a side of the cage element to elevate at least a portion of the insert.

23. An intervertebral implant for a human spine, comprising:
a cage element with a superior surface and an inferior surface, wherein the inferior surface of the cage element comprises a first opening and the superior surface of the cage element comprises a second opening;
a first insert, wherein, during use, at least a portion of the first insert is inserted at least partially into the first opening, and wherein the first insert comprises a support surface that, during use, supports at least a portion of a first vertebra below and away from the inferior surface of the cage element and inhibits movement of the first vertebra towards a second vertebra;
a second insert, wherein, during use, at least a portion of the second insert is inserted at least partially into the second opening, and wherein the second insert comprises a support surface that, during use, supports at least a portion of a second vertebra above and away from the superior surface of the cage element and inhibits movement of the second vertebra towards the first vertebra; and
an expansion member that, during use, is inserted in a third opening in the cage element to lower the support surface of the first insert below and away from the inferior surface of the cage element to support at least a portion of the first vertebra below and away from the inferior surface of the cage element and inhibit movement of the first vertebra towards a second vertebra,
wherein the expansion member when inserted in the third opening raises the support surface of the second insert above and away from the superior surface of the cage element to support at least a portion of the second vertebra above and away from the superior surface of the cage element and inhibit movement of the second vertebra towards the first vertebra.

24. The intervertebral implant of claim 23, wherein the intervertebral implant is configured such that the direction of movement of the expansion member is substantially perpendicular to the direction of movement of the first insert and the second insert.

25. The intervertebral implant of claim 23, wherein the expansion member is configured to be advanced between a superior surface of the first insert and an inferior surface of the second insert.

26. The intervertebral implant of claim 23, wherein the support surface of the first insert comprises osteoconductive mesh structure.

27. The intervertebral implant of claim 23, wherein the support surface of the second insert comprises osteoconductive mesh structure.

28. The intervertebral implant of claim 23, wherein an interior surface of the cage element comprises a raised portion configured to inhibit backout of the expansion member after insertion of the expansion member.

29. The intervertebral implant of claim 23, wherein expanding the intervertebral implant comprises increasing a height of the intervertebral implant.

30. The intervertebral implant of claim 23, wherein the expansion member comprises at least one angled portion configured to engage an angled portion of the first or second insert to facilitate insertion of the expansion member in the cage element.

31. The intervertebral implant of claim 23, wherein the support surface of the first insert comprises at least a majority of a surface of the intervertebral implant that is configured to support the first vertebra.

32. The intervertebral implant of claim 23, wherein the support surface of the second insert comprises at least a majority of a surface of the intervertebral implant that is configured to support the second vertebra.

33. The intervertebral implant of claim 23, wherein the support surface of the first insert comprises a substantially planar surface that supports at least a portion of the first vertebra above and away from the inferior surface of the cage element and inhibits movement of the second vertebra towards the first vertebra during use, and wherein the support surface of the second insert comprises a substantially planar surface that supports at least a portion of the second vertebra above and away from the superior surface of the cage element and inhibits movement of the second vertebra towards the first vertebra during use.

34. The intervertebral implant of claim 23, wherein the support surface of the first insert comprises a substantially planar surface of sufficient cross-sectional area to support the second vertebra below and away from the inferior surface of the cage element during use, and wherein the support surface of the second insert comprises a substantially planar surface of sufficient cross-sectional area to support the second vertebra above and away from the superior surface of the cage element during use.

35. The intervertebral implant of claim 23, wherein, during use, the support surface of the first insert supports at least a portion of a first vertebra below and away from the inferior surface of the cage element such that the first vertebra does not contact the inferior surface of the cage element, and the support surface of the second insert supports at least a portion of a second vertebra above and away from the superior surface of the cage element such that the second vertebra does not contact the superior surface of the cage element.

36. The intervertebral implant of claim 23, wherein the expansion member is at least partially removed from the cage element after being inserted in the third opening in the cage element to lower the support surface of the first insert below and away from the inferior surface of the cage element to support at least a portion of the first vertebra below and away from the inferior surface of the cage element and inhibit movement of the first vertebra towards a second vertebra.

37. An intervertebral implant for a human spine, comprising:
a first member comprising a first inferior surface and a first superior surface, where the first superior surface comprises a substantially planar surface configured to contact and support a first vertebra of a human spine;
a second member comprising a second inferior surface and a second superior surface, where the second inferior surface comprises a substantially planar surface configured to contact and support a second vertebra of a human spine;
a cage comprising a first opening in a superior surface of the cage and a second opening in an inferior surface of the cage, wherein, during use, the first member is inserted at least partially into the first opening and the second member is inserted at least partially in the second opening; and
an expansion element that, during use, is inserted between the first inferior surface of the first member and the second superior surface of the second member, wherein insertion of the expansion member expands the first and second members relative to one another to increase a separation distance between the first superior surface of the first member and the second inferior surface of the second member, wherein the first superior surface is expanded above the superior surface of the cage and the second inferior surface is expanded below the inferior surface of the cage, such that the distance between the first superior surface and the second inferior surface is greater than the distance between the superior surface and the inferior surface of the cage, and wherein the first superior surface supports at least a portion of the first vertebra above the superior surface of the cage and the second inferior surface supports at least a portion of the second vertebra below the inferior surface of the cage.

38. The intervertebral implant of claim 37, wherein the expansion element is at least partially removed from the cage element after being inserted between the first inferior surface of the first member and the second superior surface of the second member.

* * * * *